(12) United States Patent
Makarov et al.

(10) Patent No.: US 8,409,804 B2
(45) Date of Patent: Apr. 2, 2013

(54) ISOLATION OF CPG ISLANDS BY THERMAL SEGREGATION AND ENZYMATIC SELECTION-AMPLIFICATION METHOD

(75) Inventors: Vladimir L. Makarov, Ann Arbor, MI (US); Emmanuel Kamberov, Ann Arbor, MI (US); Brendan J. Tarrier, Whitmore Lake, MI (US)

(73) Assignee: Rubicon Genomics, Inc., Ann Arbor, MI (US)

( * ) Notice: Subject to any disclaimer, the term of this patent is extended or adjusted under 35 U.S.C. 154(b) by 1508 days.

(21) Appl. No.: 11/367,046

(22) Filed: Mar. 2, 2006

(65) Prior Publication Data

US 2007/0031858 A1   Feb. 8, 2007

Related U.S. Application Data

(60) Provisional application No. 60/704,541, filed on Aug. 2, 2005.

(51) Int. Cl.
*C12Q 1/68* (2006.01)
*C12P 19/34* (2006.01)

(52) U.S. Cl. .................................. 435/6.12; 435/91.2

(58) Field of Classification Search ............... 435/91.2, 435/6.12
See application file for complete search history.

(56) References Cited

U.S. PATENT DOCUMENTS

| | | | |
|---|---|---|---|
| 5,043,272 A | 8/1991 | Hartley | |
| 5,104,792 A | 4/1992 | Silver et al. | |
| 5,106,727 A | 4/1992 | Hartley et al. | |
| 5,405,760 A | 4/1995 | Raleigh et al. | |
| 5,514,545 A | 5/1996 | Eberwine | |
| 5,714,318 A | 2/1998 | Sagner et al. | |
| 5,731,171 A | 3/1998 | Bohlander | |
| 5,759,821 A | 6/1998 | Teasdale | |
| 5,759,822 A | 6/1998 | Chenchik et al. | |
| 5,814,444 A * | 9/1998 | Rabinovitch | 435/6 |
| 5,871,920 A * | 2/1999 | Page et al. | 435/6 |
| 5,932,451 A | 8/1999 | Wang et al. | |
| 5,948,649 A | 9/1999 | Stewart et al. | |
| 5,968,743 A | 10/1999 | Matsunaga et al. | |
| 5,994,058 A | 11/1999 | Senepathy | |
| 6,045,994 A | 4/2000 | Zabeau et al. | |
| 6,060,245 A | 5/2000 | Sorge et al. | |
| 6,107,023 A | 8/2000 | Reyes et al. | |
| 6,114,149 A | 9/2000 | Fry et al. | |

(Continued)

FOREIGN PATENT DOCUMENTS

| | | |
|---|---|---|
| EP | 0 466 520 | 1/1992 |
| EP | 0 684 315 A1 | 11/1995 |

(Continued)

OTHER PUBLICATIONS

Agarwal et al., Nucleic Acids Research 21(22), 5283-5284 (1993).*

(Continued)

*Primary Examiner* — Kenneth R. Horlick
(74) *Attorney, Agent, or Firm* — Parker Highlander PLLC

(57) ABSTRACT

The present invention concerns isolation, library preparation and selective amplification from a compositionally heterogeneous pool of DNA fragments of a fraction of molecules, such as those originating from promoter CpG islands and characterized by a high GC content. In particular, the process utilizes a heat-induced segregation of DNA molecules into GC-poor, single-stranded molecule fractions and GC-rich, double-stranded molecule fractions, with subsequent enzymatic conversion of the GC-rich, double-stranded DNA molecules into a library, and, optionally, amplification. In specific embodiments, the isolation process is used to generate promoter-enriched genomic and methylome libraries for research and diagnostic applications, for example.

29 Claims, 19 Drawing Sheets

U.S. PATENT DOCUMENTS

| | | | |
|---|---|---|---|
| 6,124,120 | A | 9/2000 | Lizardi |
| 6,214,556 | B1 | 4/2001 | Olek et al. |
| 6,280,949 | B1 | 8/2001 | Lizardi |
| 6,300,071 | B1 | 10/2001 | Vuylsteke et al. |
| 6,365,375 | B1 | 4/2002 | Dietmaier et al. |
| 6,379,932 | B1 | 4/2002 | Arnold et al. |
| 6,383,754 | B1 | 5/2002 | Kaufman et al. |
| 6,509,160 | B1 | 1/2003 | Sapolsky et al. |
| 6,521,428 | B1 | 2/2003 | Senapathy |
| 6,537,757 | B1 | 3/2003 | Langmore et al. |
| 6,605,432 | B1 | 8/2003 | Huang |
| 6,621,782 | B1 | 9/2003 | Nakane et al. |
| 6,632,611 | B2 | 10/2003 | Su et al. |
| 6,638,722 | B2 | 10/2003 | Ji et al. |
| 6,677,121 | B2 | 1/2004 | Lizardi et al. |
| 6,692,918 | B2 | 2/2004 | Kurn |
| 6,762,022 | B2 | 7/2004 | Makarov et al. |
| 6,773,886 | B2 | 8/2004 | Kaufman et al. |
| 6,794,141 | B2 | 9/2004 | Erlander et al. |
| 6,808,888 | B2 | 10/2004 | Zhang et al. |
| 6,825,010 | B2 | 11/2004 | Spier et al. |
| 2001/0021518 | A1 | 9/2001 | Goudsmit et al. |
| 2001/0046669 | A1 | 11/2001 | McCobmie et al. |
| 2002/0058250 | A1 | 5/2002 | Firth |
| 2003/0013671 | A1 | 1/2003 | Mineno et al. |
| 2003/0099997 | A1 | 5/2003 | Bestor |
| 2003/0129602 | A1 | 7/2003 | Huang |
| 2003/0143599 | A1 | 7/2003 | Makarov et al. |
| 2003/0165885 | A1 | 9/2003 | Arnold et al. |
| 2003/0186237 | A1 | 10/2003 | Ginsberg et al. |
| 2003/0232371 | A1 | 12/2003 | Bestor |
| 2004/0043416 | A1 | 3/2004 | Ji et al. |
| 2004/0063144 | A1 | 4/2004 | Lizardi |
| 2004/0132048 | A1* | 7/2004 | Martienssen et al. ............. 435/6 |
| 2004/0209298 | A1 | 10/2004 | Kamberov et al. |
| 2004/0209299 | A1 | 10/2004 | Pinter et al. |

FOREIGN PATENT DOCUMENTS

| | | |
|---|---|---|
| EP | 0 976 835 | 2/2000 |
| EP | 1 275 738 | 1/2003 |
| JP | 8173164 | 7/1996 |
| WO | WO-93/24654 A1 | 12/1993 |
| WO | WO-96/15264 | 5/1996 |
| WO | WO-97/30062 | 8/1997 |
| WO | WO-98/02575 | 1/1998 |
| WO | WO-98/15652 A1 | 4/1998 |
| WO | WO-99/28498 | 6/1999 |
| WO | WO-00/17390 | 3/2000 |
| WO | WO-01/09384 | 2/2001 |
| WO | WO-01/51661 | 7/2001 |
| WO | WO-02/06533 | 1/2002 |
| WO | WO-02/20571 | 3/2002 |
| WO | WO-02/060318 | 8/2002 |
| WO | WO-02/072772 | 9/2002 |
| WO | WO-02/101022 | 12/2002 |
| WO | WO-02/103054 | 12/2002 |
| WO | WO-03/012118 | 2/2003 |
| WO | WO-03/016546 | 2/2003 |
| WO | WO-03/025215 | 3/2003 |
| WO | WO-03/027259 | 4/2003 |
| WO | WO-03/035860 | 5/2003 |
| WO | WO-03/050242 | 6/2003 |
| WO | WO-03/087774 | 10/2003 |
| WO | WO-2005/090607 | 9/2005 |

OTHER PUBLICATIONS

Cusi et al., BioTechniques 12(4), 502,504 (1992).*
Adam et al., "Cross-linking of the p55 Tumor Necrosis Factor Receptor cytoplasmic Domain by a dimeric Ligand Induces Nuclear Factor-κB and Mediates Cell Death," *J. Biol. Chem.*, 270(29): 17482-17487, 1995.
Ailenberg et al., "Controlled Hot Start and Improved Specificity in Carrying Out PCR Utilizing Touch-Up and Loop Incorporated Primers (TULIPS)," *BioTechniques*, 29: 1018-1024, 2000.
Badal et al., "CpG Methylation of Human Papillomavirus Type 16 DNA in Cervical Cancer Cell Lines and in Clinical Specimens: Genomic Hypomethylation Correlates with Carcinogenic Progression," *Journal of Virology*, 77(11): 6227-6234, 2003.
Baldini et al., "Chromosomal assignment of human YAC clones by fluorescence in situ hybridization: use of single-yeast-colony PCR and multiple labeling," *Genomics*, 14: 181-184, 1992.
Barbaux et al., "Use of degenerate oligonucleotide primed PCR (DOP-PCR) for the genotyping of low-concentration DNA samples," *J Mol Med*, 79: 329-332, 2001.
Beekman et al., "A powerful and rapid approach to human genome scanning using small quantities of genomic DNA," *Genet. Res. Camb.*, 77: 129-134, 2001.
Bellizzi et al., "A procedure for cloning genomic DNA fragments with increasing thermoresistance," *Gene*, 219: 63-71, 1998.
Bohlander et al., "A Method for the Rapid Sequence-Independent Amplification of Microdissected Chromosomal Material," *Genomics*, 13:1322-1324, 1992.
Breen et al., "YAC mapping by FISH using Alu-PCR-generated probes," *Genomics*, 13: 726-730, 1992.
Broude, "Stem-loop oligonucleotides: a robust tool for molecular biology and biotechnology," *Trends in Biotechnology*, 20: 249-256, 2002.
Buchanan et al., "Long DOP-PCR of rare archival anthropological samples," *Hum. Biol.*, 72(6): 911-25, 2000.
Campbell et al., "The effect of divalent cations on the mode of action DNase 1. The initial reaction products produced from covalently closed circular DNA," *J. Biol. Chem.*, 255: 3726-3735, 1980.
Champoux, "DNA Topoisomerases: Structure, Function, and Mechanism," *Annu. Rev. Biochem.*, 369-413, 2001.
Chang et al., "PCR amplification of chromosome-specific DNA isolated from flow cytometry-sorted chromosomes," *Genomics*, 12:307-312, 1992.
Chen et al., "Methylation Target Array for Rapid Analysis of CpG Island Hypermethylation in Multiple Tissue Genomes," *Am. J. Pathol*, 163(1): 37-45, 2003.
Cheng et al., "Degenerate oligonucleotide primed-polymerase chain reaction and capillary electrophoretic analysis of human DNA on microchip-based devices," *Anal. Biochem.*, 257(2): 101-6, 1998.
Cheung et al., "Whole genome amplification using a degenerate oligonucleotide primer allows hundreds of genotypes to be performed on less than one nanogram of genomic DNA," *Proc. Natl. Acad. Sci. USA*, 93: 14676-14679, 1996.
Chotai et al., "A rapid, PCR based test for differential molecular diagnosis of Prader-Willi and Angelman syndromes," *J. Med. Genet.*, 35: 472-475, 1998.
Clay et al., "Using analytical ultracentrifugation to study compositional variation in vertebrate genomes," *Eur. Biophys. J.*, 32: 418-426, 2003.
Cross et al., "CpG island libraries from human chromosomes 18 and 22: landmarks for novel genes," *Mammalian Genome*, 11: 373-383, 2000.
Cross et al., "Isolation of CpG islands from large genomic clones," *Nucleic Acid Res.*, 27: 2099-2107, 1999.
Dean et al., "Comprehensive human genome amplification using multiple displacement amplification," *PNAS*, 99(8): 5261-5266, 2002.
DeRisi Laboratory, Dept. of Biochemistry and Biophysics, Univ. of California at San Francisco, "Randon DNA Amplification. Directions for amplifying products for printing arrays," 2001.
Frigola et al., "Methylome profiling of cancer cells by amplification of inter-methylated sites (AIMS)," *Nucleic Acids Res.*, 30(7): e28, 2002.
Fu et al., "Sequencing Double-Stranded DNA by Strand Displacement," *Nucleic Acids Research*, 25(3): 677-679, 1997.
Grace et al., "Degradable dUMP Outer Primers in Merged Tandem (M/T)-Nested PCR: Low- and Single-Copy DNA Target Amplification," *Analytical Biochemistry*, 263: 85-92, 1998.
Grothues et al., "PCR amplification of megabase DNA with tagged random primers (T-PCR)," *Nucleic Acids Res.*, 21(5):1321-1322, 1993.
Guan et al., "Generation of band-specific painting probes from a single microdissected chromosome," *Human Mol. Genet.*, 2(8): 1117-1121, 1993.

Guilfoyle et al., "Ligation-mediated PCR amplification of specific fragments from a Class-II restriction endonuclease total digest," *Nucleic Acids Res.*, 25(9):1854-1858, 1997.

Hadano et al., "Laser microdissection and single unique primer PCR allow generation of regional chromosome DNA clones from a single human chromosome," *Genomics*, 11:364:373, 1991.

Hawkins et al., "Whole genome amplification—applications and advances," *Current Opinion in Biotechnology*, 13: 65-67, 2002.

Huang et al., "Methylation profiling of CpG islands in human breast cancer cells," *Human Molecular Genetics*, 8(3): 459-470, 1999.

Igloi, "Substrate properties of fluorescent ribonucleotides in the terminal transferase-catalyzed labeling of DNA sequencing primers," *Biotechniques*, 21: 1084-1092, 1996.

Invitrogen Corporation, Carlsbad, California 92008, TOPO TA Cloning. Version P 051302 / 25-0184, pp. 1-32, 1999-2002.

Jones et al., "Amplification of 4-9-кb Human Genomic DNA Flanking a Known Site Using a Panhandle PCR Variant," *BioTechniques*, 23: 132-138, 1997.

Kaboev et al., "PCR hot start using primers with the structure of molecular beacons (hairpin-like structure)," *Nucleic Acids Research*, 28(21): e94, 2000.

Kaiser et al., "Specific-primer-directed DNA sequencing using automated fluorescent detection," *Nucleic Acids Res.*, 17: 6087-6102, 1989.

Kao et al., "Chromosome microdissection and cloning in human genome and genetic disease analysis," *Proc. Natl. Acad. Sci. USA*, 88:1844-1848, 1991.

Kempf et al., "Improved stimulation of human dendritic cells by receptor engagement with surface-modified microparticles," *J Drug Target*, 2003.

Kikuchi et al., "Expression profiles of non-small cell lung cancers on cDNA microarrays:Identification of genes for prediction of lymph-node metastasis and sensitivity to anti-cancer drugs," *Oncogene*, 2192-2205, 2003.

Kilger et al., "Direct DNA sequence determination from total genomic DNA," *Nucleic Acids Research*, 25(10): 2032-2034, 1997.

Kinzler et al., "Whole genome PCR: application to the identification of sequences bound by gene regulatory proteins," *Nucleic Acids Research*, 17(10): 3645-3653, 1989.

Kittler et al., "A Whole Genome Amplification Method to Generate Long Fragments from Low Quantities of Genomics DNA", *Anal. Biochem.*, 300: 237-244, 2001.

Klein et al., "Comparative genomic hybridization, loss of heterozygosity, and DNA sequence analysis of single cells," *Proc. Natl. Acad. Sci. USA*, 96: 4494-4499, 1999.

Ko et al. "Unbiased amplification of highly complex mixture of DNA fragments by 'lone linker'—tagged PCR," *Nucleic Acids Res.*, 18: 4293-4294, 1990.

Kong et al., "PCR hot-start using duplex primers," *Biotechnology Letters*, 26: 277-280, 2004.

Kusov et al., "A new G-tailing method for the determination of the poly(A) tail length applied to hepatitis A virus RNA," *Nucleic Acids Research*, 29(12): e57, 2001.

Kuukasjarvi et al., "Optimizing DOP-PCR for Universal Amplificatino of Small DNA Samples in Comparative Genomic Hybridization," *Genes, Chromosomes & Cancer*, 18: 94-101, 1997.

Lengauer et al., "Fluorescence in situ hybridization of YAC clones after Alu-PCR amplification," *Genomics*, 13: 826-828, 1992.

Lerman et al., "Sequence-determined DNA separations," *Annu. Rev. Biophys. Bioeng.*, 13: 399-423, 1984.

Lisitsyn et al., "Cloning the differences between two complex genomes," *Science*, 259: 946-951, 1993.

Lucito et al., "Genetic analysis using genomic representations," *Proc. Natl. Acad. Sci. USA*, 95: 4487-4492, 1998.

Ludecke et al., "Cloning defined regions of the human genome by microdissection of banded chromosomes and enzymatic amplification," *Nature*, 338(6213): 348-50, 1989.

Makrigiorgos et al., "A PCR-based amplification method retaining the quantitative difference between two complex genomes," *Nature Biotechnology*, 20: 937-939, 2002.

McGrath et al., "Sequence analysis of DNA randomly amplified from the *Saccharomyces cerevisiae* genome," *Molecular and Cellular Probes,*, 12: 397-405, 1998.

Melief et al., "Effective theraputic anticancer vaccines based on precision guiding of cytolytic T lymphocytes," *Immunol Rev.*, 2002.

Miyashita et al., "A mouse chromosome 11 library generated from sorted chromosomes using linker-adapter polymerase chain reaction," *Cytogenet. Cell Genet.*, 66: 454-57, 1994.

Mullis et al., "Specific enzymatic amplification of DNA in vitro: the polymerase chain reaction," Cold Spring Harbor Symp., 263-273, 1986.

Nelson et al., "Alu-primed polymerase chain reaction for regional assignment of 110 yeast artificial chromosome clones from the human X chromosome: identification of clones associated with a disease locus," *PNAS*, 88: 6157-6161, 1991.

Nishigaki et al., "Whole genome sequence-enabled prediction of sequences performed for random PCR products of *Escherichia coli,*" *Nucleic Acids Research*, 28(9): 1879-1884, 2000.

PCT International Preliminary Examination Report, PCT NL01 00020, dated Mar. 25, 2003.

PCT International Search, PCT-NL01 00020, dated Jul. 18, 2002.

Perou et al., "Molecular Portraits of Human Breast Tumors," *Nature*, 406, 2000.

Pfeifer, "Chromatin structure analysis by ligation-mediated and terminal transferase-mediated polymerase chain reaction," *Methods Enzymol.*, 304: 548-571, 1999.

Phillips et al., "Antisense RNA Amplification: A Linear Amplification Method for Analyzing the mRNA Population from Single Living Cells," *Methods: Acompanion to Methods in Enzymology* 10, Article No. 0104, 283-288, 1996.

Reyes, Gregory R., et al.; Sequence-independent, single-primer amplification (SISPA) of complex DNA populations; Molecular and Cellular Probes 5: 473-481, 1991.

Riccelli et al., "Hybridization of single-stranded DNA targets to immobilized complementary DNA probes: comparison of hairpin versus-linear capture probes," *Nucleic Acids Research*, 29: 996-1004, 2001.

Rose et al., "Consensus-degenerate hybrid oligonucleotide primers for amplification of distantly related sequences," *Nucleic Acids Research*, 26(7): 1628-1635, 1998.

Sanchez-Cespedes et al., "Degenerate oligonucleotide-primed PCR (DOP-PCR): evaluation of its reliability for screening of genetic alterations in neoplasia," *Biotechniques*, 25(6): 1036-8, 1998.

Sato et al., "Combination of monocyte-derived dendritic cells and activated T cells which express CD40 ligand: a new approach to cancer immunotherapy," *Cancer Immunol. Immunother.*, 53(1): 53-61, 2004.

Saunders et al., "PCR amplification of DNA microdissected from a single polytene chromosome band: A comparison with conventional microcloning," *Nucleic Acids Res.*, 17: 9027-9037, 1989.

Schiefermayr et al., "Degradation of DNA sequencing primers by a terminal transferase-associated exonuclease," *Anal. Biochem.*, 230: 180-182, 1995.

Schmidt et al., "CapSelect: A highly sensitive method for 5' CAP-dependant enrichment of full-length cDNA in PCR-mediated analysis of mRNAs," *Nucleic Acids Research*, 27(21), 1999.

Sharrrocks, Andrew D., et al., "The Design of Primers for PCR", *PCR Technology Current Innovations*, Chapter 2, 5-11, 1994.

Shiraishi et al., "Isolation of DNA fragments associated with methylated CpG islands in human adenocarcinomas of the lung using a methylated DNA binding column and denaturing gradient gel electrophoresis," *Proc. Natl. Acad. Sci. USA*, 96: 2913-2918, 1999.

Shiraishi et al., "Preferential isolation of DNA fragments associated with CpG islands," *Proc. Natl. Acad. Sci. USA*, 92: 4229-4233, 1995.

Shiraishi et al., "The isolation of CpG islands from human chromosomal regions 11q13 and Xp22 by segregation of partly melted molecules," *Nucleic Acid Res.*, 26: 5544-5550, 1998.

Shyamala et al., "Genome walking by single-specific-primer polymerase chain reaction: SSP-PCR," *Gene*, 84: 1-8, 1989.

Siebert et al., "An improved PCR method for walking in uncloned genomic DNA," *Nucleic Acids Res.*, 23: 1087-1088, 1995.

Smith, "Ligation-mediated PCR of restriction fragments from large DNA molecules," *PCR Methods Appl.*, 2(1):21-7, 1992.

Smith et al., "Automated differential display using a flourescently labeled universal primer," *Biotechniques*, 23(2): 274-279, 1997.

Smith et al., "Single primer amplification (SPA) of cDNA for microarray expression analysis," *Nucleic Acids Research*, 31(3): e9, 2003.

Snabes et al., "Preimplantation single-cell analysis of multiple genetic loci by whole-genome amplification," *Proc. Natl. Acad. Sci. USA (Genetics)*, 91: 6181-6185, 1994.

Strichman-Almashanu et al., "A Genome-Wide Screen for Normally Methylated Human CpG Islands That Can Identify Novel Imprinted Genes," *Genome Research*, 12(4): 543-54, 2002.

Studier et al., "Relationships among Different Strains of T7 and among T7-Related Bacteriophages," 70-84, 1979.

Sutcliffe et al., "PCR amplification and analysis of yeast artificial chromosomes," *Genomics*, 13: 1303-1306, 1992.

Tanabe et al., "Evaluation of a Whole-Genome Amplification Method Based on Adaptor-Ligation PCR of Randomly Sheared Genomic DNA," *Genes, Chromosomes & Cancer*, 38: 168-176, 2003.

Telenius et al., "Degenerate Oligonucleotide-Primed PCR: General Amplification of Target DNA by a Single Degenerate Primer," *Genomics*, 13: 718-725, 1992.

Toyota et al., "Methylated CpG Island Amplification for Methylation Analysis and Cloning Differentially Methylated Sequences," *Methods in Molecular Biology*, 200: 101-10, 2002.

VanDevanter et al., "Pure chromosome-specific PCR libraries from single sorted chromosome," *Proc. Natl. Acad. Sci. USA*, 91: 5858-5862, 1994.

Vooijs et al., "Libraries for each human chromosome, constructed from sorter-enriched chromosomes by using linker-adaptor PCR," *Am. J. Hum. Genet*, 52: 586-597, 1993.

Wells et al., "Comprehensive chromosomal analysis of human preimplantation embryos using whole genome amplification and single cell comparative genomic hybridization," *Molecular Human Reproduction*, 6(11): 1055-1062, 2000.

Wells et al., "Detailed chromosomal and molecular genetic analysis of single cells by whole genome amplification and comparative genomic hybridisation," *Nucleic Acids Res.*, 27(4): 1214-1218, 1999.

Wesley et al., "Cloning regions of the *Drosophila* genome by microdissection of polytene chromosome DNA and PCR with non-specific primer," *Nucleic Acids Res.*, 18(3): 599-603, 1990.

Whitcombe et al., "Detection of PCR products using self-probing amplicons and fluorescence," *Nat. Biotechnol.*, 17: 804-807, 1999.

Wold, "Replication Protien A: A-Heterotrimeric, Single-Stranded DNA-Binding Protein Required for Eukaryotic DNA Metabolism," *Annu. Rev. Biochem.*, 61-92, 1997.

Wong et al., "Use of tagged random hexamer amplification (TRHA) to clone and sequence minute quantities of DNA-application to a 180 κb plasmid isolated from sphingmonas F199," *Nucleic Acids Research,*, 24: 3778-3783, (1996).

Yan et al., "Dissecting Complex Epigenetic Alterations in Breast Cancer Using CpG Island Microarrays," *Cancer Res.*, 61: 8375-8380, 2001.

Zhang et al., "Whole genome amplification from a single cell: Implications for genetic analysis," *Proc. Natl. Acad.*, 89: 5847-5851, 1992.

Zheleznaya et al., "PCR Fragmentation of DNA," *Biochemistry* (Moscow), 64(4): 447-453, 1999.

Eichler et al., "CAGGG repeats and the pericentromeric duplication of the hominoid genome," *Genome Research*, 9:1048-1058, 1999.

Meneveri et al., "Analysis of GC-rich repetitive nucleotide sequences in great apes," *J. Mol. Evol.*, 40:405-412, 1995.

Nonin-Lecomte et al., "Self-organisation of an oligodeoxynucleotide containing the G- and C-rich stretches of the direct repeats of the human mitochondrial DNA," *Biochimie*, 87:725-735, 2005.

Oei et al., "Clusters of regulatory signals for RNA polymerase II transcription associated with Alu family repeats and CpG islands in human promoters," Genomics, 83:873-882, 2004.

* cited by examiner

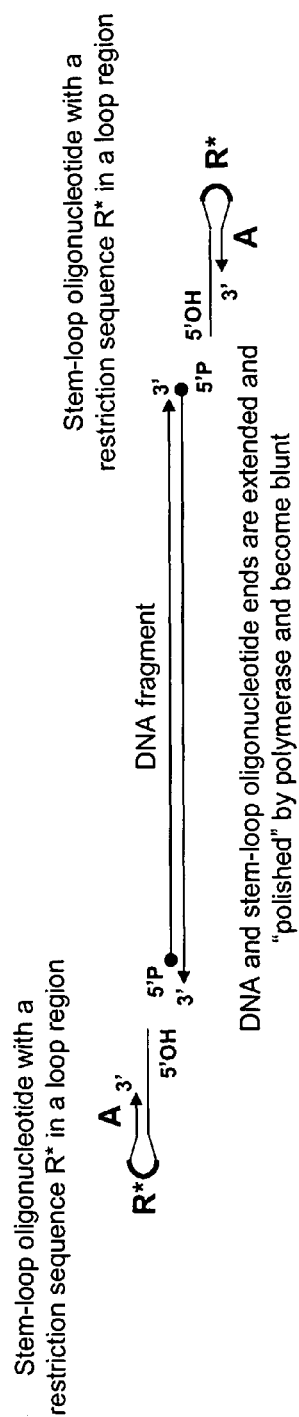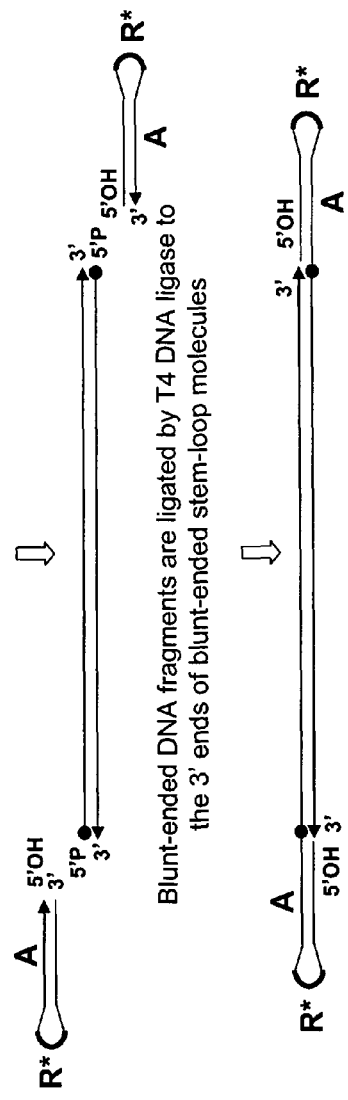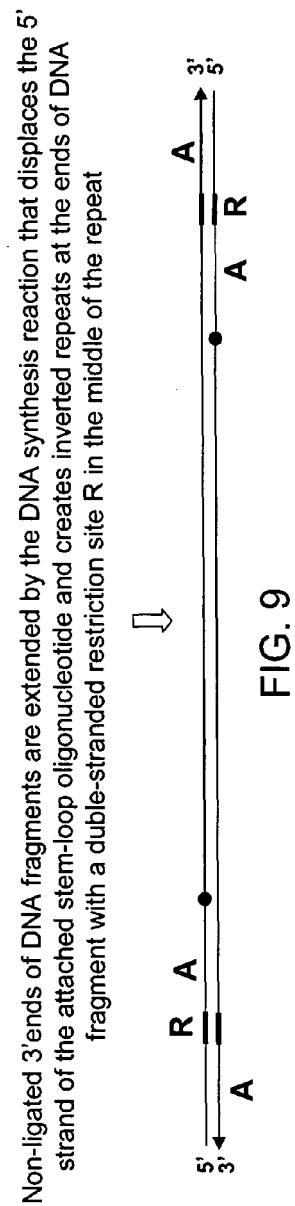
FIG. 9

SEQUENCE LISTING

```
<160> NUMBER OF SEQ ID NOS: 26

<210> SEQ ID NO 1
<211> LENGTH: 12
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 1
ccaaacacac cc                                                            12

<210> SEQ ID NO 2
<211> LENGTH: 18
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 2
ggtttgtgtg ggttgtgt                                                      18

<210> SEQ ID NO 3
<211> LENGTH: 42
<212> TYPE: DNA
<213> ORGANISM: Artificial Sequence
<220> FEATURE:
<223> OTHER INFORMATION: Description of Artificial Sequence: Synthetic
      Primer
<220> FEATURE:
<221> NAME/KEY: modified_base
<222> LOCATION: (1)..(16)
<223> OTHER INFORMATION: t = t/u

<400> SEQUENCE: 3
tgtgttgggu gugtgtgguu uuuuccacac acacccaaca ca                           42

<210> SEQ ID NO 4
<211> LENGTH: 18
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 4
ccacacacac ccaacaca                                                      18

<210> SEQ ID NO 5
<211> LENGTH: 19
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 5
cgggtcggga agcggagag                                                     19

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
```

-continued

Primer

<400> SEQUENCE: 6
tggcgggctg caccaataca g                                       21

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 7
gggtgggagg aagcatcgtc                                         20

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 8
ggtctccagc atctccacga a                                       21

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 9
cccttggttt ccgtggcaac                                         20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 10
ctccccaggg ttcacaacgc                                         20

<210> SEQ ID NO 11
<211> LENGTH: 19
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 11
cctctgccag gttcggtcc                                          19

<210> SEQ ID NO 12
<211> LENGTH: 23
<212> TYPE: DNA
<213> ORGANISM: Artificial Sequence
<220> FEATURE:
<223> OTHER INFORMATION: Description of Artificial Sequence: Synthetic
      Primer

```
<400> SEQUENCE: 12
gctgcgtgcc accaaaactt gtc                                          23

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 13
tgggaaagag ggaaaggctt c                                            21

<210> SEQ ID NO 14
<211> LENGTH: 19
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 14
ccccagtgct gagtcacgg                                               19

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 15
gcccaaagcc agcgaagcac                                              20

<210> SEQ ID NO 16
<211> LENGTH: 19
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 16
cgccacagag gtcgcacca                                               19

<210> SEQ ID NO 17
<211> LENGTH: 18
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 17
gctagagggt caccgcgt                                                18

<210> SEQ ID NO 18
<211> LENGTH: 22
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 18
```
ctgaactgac ttccgcaagc tc                                            22

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 19
agaactggct ctcggaagcg                                               20

<210> SEQ ID NO 20
<211> LENGTH: 19
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 20
gggagcagag ggggtagtc                                                19

<210> SEQ ID NO 21
<211> LENGTH: 23
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 21
gggcatcagg aaggagtttc gac                                           23

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 22
tcgccagtat ccacgctcaa                                               20

<210> SEQ ID NO 23
<211> LENGTH: 19
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 23
gcttcctgga cacgctggt                                                19

<210> SEQ ID NO 24
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 24
tctatgcggg catggttact g                                             21

```
<210> SEQ ID NO 25
<211> LENGTH: 22
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 25
caagcttcct ttccgtcatg cc                                              22

<210> SEQ ID NO 26
<211> LENGTH: 19
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 26
agcaccacca gcgtgtcca                                                  19
```

ISOLATION OF CPG ISLANDS BY THERMAL SEGREGATION AND ENZYMATIC SELECTION-AMPLIFICATION METHOD

The present invention claims priority to U.S. Provisional Patent Application Ser. No. 60/704,541, filed Aug. 2, 2005, which is incorporated by reference herein in its entirety.

FIELD OF THE INVENTION

The present invention generally concerns the fields of molecular biology and cellular biology. In particular, the present invention regards selection of molecules with a specific base composition, preparation of molecules for a library, and amplification of selected molecules, such as for amplification of a GC-rich DNA fraction (CpG islands), utilizing novel selection reactions.

BACKGROUND OF THE INVENTION

Human DNA has complex genomic organization, and it is characterized by large variations in DNA base composition, usually described in terms of GC content, or % GC (FIG. 1). GC is defined as a molar fraction of guanine and cytosine in a genome, molecule or DNA fragment, for example. The GC distribution and compositional heterogeneity of human DNA was initially discovered and analyzed by analytical ultracentrifugation in CsCl gradients (Guttann, T., et al.,(1976); Clay, O., et al., (2003)) and later confirmed by DNA sequence analysis (Clay, O., et al., 2001; Takai, D., and Jones, P. A. (2002)]. Variations in DNA base composition are linked to variations in gene density so that the GC-rich regions are usually 10-20 times higher in genes than GC-poor regions.

The CpG dinucleotides play a very special role in human and all other mammalian organisms by providing a target for DNA methylation. DNA methylation is the post-synthetic modification that introduces a methyl group to carbon-5 of cytosine and creates 5 mC, the 5th DNA base. The CpG dinucleotides are distributed in a non-random fashion in human genomic DNA. The frequency with which CpG dinucleotides are found in a genome is much lower than expected from an average human genome G+C content, except for CpG clusters or "CpG islands" (Cross, S. H., and Bird, A. P., (1995)). The CpG islands are present in the promoter, and exonic regions of approximately 40% of mammalian genes. They vary in size from 200 bp up to 2.5 kb and constitute about 1-2% of the total human genome (see FIG. 1, a black region on the CpG distribution diagram). The average GC content of human CpG islands is about 65% (FIG. 2).but some CpG islands are extremely GC-rich and have as much as 75-80% GC content (Takai, D., and Jones, P. A., (2002)). There are about 30,000 CpG islands in the human genome, and the islands are normally unmethylated. In contrast, other regions of the genome contain few CpG dinucleotides, and these are largely methylated. Multiple findings support the idea that the transcription of genes associated with promoter CpG islands is active when these regions are in unmethylated state, and it is inhibited by promoter methylation. Methylation of promoter CpG islands plays an important role in the regulation of gene expression, development, tissue-specific gene function, genomic imprinting, and X-chromosome inactivation (see U.S. patent application Ser. No. 11/071,864 and references therein, all of which are incorporated by reference herein in their entirety). Aberrant methylation patterns of CpG islands have been associated with ageing, inflammation, infectious diseases, autoimmune conditions, and carcinogenesis (see U.S. patent application Ser. No. 11/071,864 and references therein, all of which are incorporated by reference herein in their entirety).

Despite the important biological role of CpG islands and their close association with genes and gene regulation, only a few methods have been developed for purification and isolation of GC-rich DNA, and specifically, CpG islands.

Bernardi and his coworkers (Clay, O., et al., (2003)) used DNA fractionation by centrifugation in $Cs_2SO_4$ density gradients containing 3,6-bis(acetatomercurimethyl)dioxane and discovered a class of DNA with very high GC content that was particularly rich in genes and interspersed repetitive sequences.

Bird and his colleagues developed the methyl-CpG binding domain (MBD) column chromatography method (Cross, S. H., et al., (1999); Cross, S. H., et al., (2000)). In this method, DNA was digested to completion with MseI restriction enzyme, methylated at all CpGs using CpG methylase (NEB), and fractionated on a column containing $Ni^{2+}$-NTA-agarose coupled with the histidine-tagged methyl-CpG binding domain protein purified from crude bacterial extracts. Eluted DNA fragments were cloned and sequenced. The method was successfully used for bulk purification and analysis of CpG islands from whole genomes (Cross, S. H., et al., (1999); Cross, S. H., et al., (2000)) and from cosmid, BAC, and PAC DNA clones (Cross, S. H., et al., (1999); Cross, S. H., et al., (2000)).

Lerman, L. S. et al., (1984) introduced the idea of analysis of DNA duplex stability using agarose gel electrophoresis of heated DNA.

Shiraishi and coworkers developed a method for preferential isolation of DNA fragments associated with CpG islands by segregation of partly melted molecules (SPM). The method is conceptually simple and uses denaturant gradient gel electrophoresis to separate DNA molecules digested with restriction endonucleases. For DNA fragments derived from the edge of CpG islands, stable partly melted molecules would be expected. When subjected to denaturing gradient gel electrophoresis, such partially melted DNA fragments are differentially retarded and retained in the gradient, while molecules with lower GC content are run off the gel. The SPM method (Shiraishi, M., et al., (1995); Shiraishi, M., et al., (1998)) and the combination of MBD column chromatography and SPM (Shiraishi, M., et al., (1998); Shiraishi, M., et al., (1999)) were used to identify and isolate methylated CpG islands in human cancer cells.

Bellizzi, D., et al. (1998) used exposure of DNA fragments produced by restriction cleavage or sonication to increasing temperatures to clone thermoresistant DNA duplexes.

Although some of the methods described above have been useful for isolation, characterization and understanding the role of promoter CpG islands in normal and cancer cells, they become cumbersome in applications that involve multiple DNA samples, such as cancer diagnostics (based on analysis of promoter CpG islands hypermethylation) or high throughput DNA methylation marker discovery by hybridization to a promoter micro-array. The present invention overcomes these problems and describes a simple method for enrichment, purification, and amplification of CpG islands. The method utilizes heat treatment and enzymatic selection (rather than chromatographic methods) for isolation and in vitro amplification of GC-rich DNA and can be easily implemented in diagnostic applications and high throughput screening assays, for example.

SUMMARY OF THE INVENTION

The present invention is directed to a system and method for selection of molecules with a specific base composition, such as molecules with a high GC content, preparing selected molecules for a library, and amplifying them by utilizing known sequences on the molecules.

In certain aspects of the invention, DNA is segregated into single stranded and double stranded forms by heating to a DNA melting zone temperature and then cooling, wherein a library is prepared from the heat-resistant GC-rich double stranded DNA fraction, which may be optionally amplified; in specific embodiments the amplification does not comprise cloning. In additional specific embodiments, a plurality of DNA molecules having a fraction of molecules that are GC-poor and having a fraction of molecules that are GC-rich is exposed to heat, wherein the molecules from the GC-poor fraction are denatured into single stranded molecules, such as substantially fully denatured, and wherein the molecules from the GC-rich fraction may not be denatured or denatured only in part. Upon cooling of each fraction, molecules from the GC-poor fraction renature substantially incompletely, whereas molecules from the GC-rich fraction renature substantially completely. Following this, the molecules from the GC-poor fraction are unsuitable for amplification, whereas the molecules from the GC-rich fraction are suitable for amplification.

In certain aspects, high molecular weight DNA is digested with an enzyme, such as a restriction enzyme, followed by heating of the DNA to a certain melting zone temperature and cooling of the DNA. End-specific adaptors are ligated to the ends of the thermo-resistant dsDNA fragments to generate adaptor-ligated molecules, and the adaptor-ligated molecules, which may be referred to as a library, are incubated with one or more methylation-sensitive restriction enzymes; the mixture may be referred to as a methylome library. The GC-enriched library is amplified, such as by polymerase chain reaction. In specific embodiments, the 3' end of the adaptor-ligated molecules are subjected to extension by a DNA polymerase prior to incubation with one or more methylation-sensitive enzymes. In alternative embodiments, the adaptors are ligated to the ends, such as the 5' ends, of the DNA fragments prior to heating of the DNA.

In other certain aspects, naturally degraded DNA (for example, cell-free serum, plasma, or urine DNA), or nuclease-treated DNA, is subjected to modification such that the ends are polished. The DNA is heated to a certain melting zone temperature, followed by cooling. Blunt-end adaptors are ligated to the ends of thermo-resistant dsDNA fragments. The adaptor-ligated fragments, which may be referred to as a library, are incubated with one or more methylation-sensitive restriction enzymes, and may be referred to as a methylome library. This may be followed by amplification of the GC-enriched library, such as by polymerase chain reaction. In specific embodiments, the 3' end adaptor-ligated molecules are subjected to extension by a DNA polymerase prior to incubation with one or more methylation-sensitive enzymes. In alternative embodiments, the blunt-end adaptors are ligated to the ends, such as the 5' ends, of the DNA fragments prior to heating of the DNA.

In particular, the present invention greatly reduces the complexity of the prepared library by suppressing amplification of molecules with a low and medium GC content and allowing amplification of molecules only with a high GC content. The enrichment process is achieved by heat-denaturing a majority of the DNA molecules except for a small fraction of molecules that have an increased GC content, which retains a substantially unchanged double stranded conformation upon heating/cooling, followed by enzymatically selecting the double-stranded DNA fraction, including preparation and amplification of a library from the heat-resistant DNA fraction. The selected and amplified DNA molecules can constitute from about 50% to about 1% of all molecules and result in about 2 to about 100 fold enrichment of a selected DNA fraction.

A skilled artisan recognizes that denaturation (also referred to as "melting") is an equilibrium process that can be driven to completion or reversed depending upon at least the temperature (and/or the pressure, pH, or other conditions). For a given temperature, a fraction of the DNA that is GC-poor will melt completely, another fraction that is GC-rich will never melt, and yet a third fraction (with intermediate GC content) will be in a state of partial melting (or equilibrium). If the temperature drops, this partially melted fraction will re-anneal. If the temperature goes up, it will completely melt. These differences in the GC content are the basis for the thermal enrichment in the invention. It is noted in the art that the shorter the DNA, the more pronounced the effect of GC content on the melting. The GC-rich fraction of the genome (CpG islands and some repeats) will melt at about 10° C. higher temperature than the GC-poor DNA providing the genomic DNA is fragmented to suitable size (about 50 to 3000 bases, for example). In specific embodiments, denaturing can be categorized according to the fraction of the DNA that is denatured at a given temperature; for example, the categories may include the following: substantially denatured; partially denatured (intermediate state), and substantially non-denatured DNA. Again, the intermediate category may go to denaturing or back to renaturing if, for example, the temperature changes. Thus, the ratio between these three categories will vary as a function of the temperature (and/or pressure, pH, etc.).

In particular embodiments, the present invention utilizes a DNA ligase and an adaptor-DNA ligation reaction to select all double-stranded molecules that survive thermal incubation and convert them into an amplifiable DNA library. Heat-denatured DNA molecules become very inefficient templates for the ligation reaction catalyzed by DNA ligase, and as a result become substantially lost (reduced) during amplification.

In one embodiment of the invention, there is a DNA end-polishing step preceding heating and subsequent selective ligation of the blunt end adaptor to the heat-resistant (GC-rich) blunt end DNA fraction.

In another embodiment of the invention, DNA fragments generated by restriction enzyme digestion are heated and then selectively ligated to adaptors with a compatible end structure.

In some embodiments of the invention, the selective post-heating ligation reaction involves both strands of DNA molecules and adaptors. In this case, no additional 3' end extension is necessary to complete the selection process and the library preparation.

In some embodiments of the invention, the selective post-heating ligation reaction involves only one DNA strand, specifically, the 5' end of DNA molecules and the 3' end of adaptors. In this case, an additional 3' end extension DNA synthesis is necessary to complete the selection process and the library preparation.

In particular embodiments, the present invention utilizes the 3' end extension DNA synthesis as a step to select for the heat-resistant GC-rich DNA fraction. In this case, the thermal incubation step occurs after the adaptor-DNA ligation reaction that involves only one DNA strand, specifically, the 5' end of DNA molecules and the 3' end of adaptors. Only the heat-resistant GC-rich DNA fraction would retain a double-stranded structure and the ability to complete the library preparation by extending the 3' ends of dsDNA molecules into the adaptor region.

In particular embodiments, the present invention utilizes a single strand-specific endonuclease such as S1 nuclease, P1 nuclease, Mung bean nuclease, or a combination or mixture thereof, to efficiently degrade all single-stranded GC-poor DNA generated by thermal incubation while leaving intact only the heat-resistant GC-rich DNA fraction.

In one particular embodiment, the exposure of the DNA to heat and subsequent single strand-specific nuclease treatment is preceded by the library preparation and amplification.

In other particular embodiments, the thermal incubation and subsequent single strand-specific nuclease treatment are applied to a DNA library with already attached adaptors of known sequence, or even to a library with attached adaptors that had been amplified. In the latter case, the selection is achieved by re-amplification of the heat- and nuclease-treated library.

In particular embodiments, the present invention utilizes a special stem-loop oligonucleotide and an inverted repeat adaptor design with a cleavable restriction site generated during the adaptor attachment that allows implementation of the thermal enrichment-selection process to the DNA library with inverted repeat adaptors (see, for example, U.S. patent application Ser. No. 11/071,864 and U.S. Provisional Patent Application Ser. No. 60/704,932, both of which are incorporated by reference herein in their entirety). This selection process uses two additional enzymatic reactions: restriction enzyme digestion and DNA polymerization. The selection and enrichment of the GC-rich DNA fraction occurs by processing of all heat-resistant double-stranded molecules into amplifiable DNA units by a restriction digestion of the adaptors and elimination of their inverted repeat structure, and by conversion of all denatured DNA molecules into the stem-loop structures that are resistant to PCR amplification.

In specific aspects of the invention, a library prepared with ligation of stem-loop adaptors to DNA molecules is heat denatured such that those library molecules (which may be referred to herein as amplicons) having low and medium GC content are denatured by heat, whereas subsequent cooling generates the hairpin structure at their ends. However, GC-rich amplicons remain substantially double stranded. A DNA polymerase then converts denatured, GC-poor amplicons into long hairpin-like molecules. Restriction enzyme digestion removes palindromes from both ends of the GC-rich amplicons and from one end of the hairpin-like molecules. Following this, polymerase chain reaction amplifies the GC-rich amplicons, whereas hairpin-like amplicons originated from GC-poor DNA fragments remain resistant to amplification.

In particular embodiments, the present invention utilizes thermal enrichment processes to produce GC-enriched Methylome libraries for subsequent research and/or diagnostic applications to analyze the methylation status of CpG islands, for example (see, for example, U.S. patent application Ser. No. 11/071,864 and U.S. Provisional Patent Application Ser. No. 60/704,932, both of which are incorporated by reference herein in their entirety).

In one particular embodiment, the GC-enrichment step is introduced during the multi-step Methylome library synthesis, and before the library amplification, while in another particular embodiment the GC-enrichment step is performed after the library amplification.

In one particular embodiment, the GC-enrichment step is introduced right after the one-step Methylome library synthesis, but before the library amplification.

In some embodiments, the present invention utilizes thermal enrichment protocols to produce GC-enriched Whole Genome libraries for subsequent research and/or diagnostic applications, for example.

In one embodiment of the invention, there is a method of amplifying a plurality of amplifiable DNA molecules, comprising providing a plurality of DNA molecules, said plurality having molecules comprising one or more regions that are GC-poor and having molecules comprising one or more regions that are GC-rich; subjecting the plurality of DNA molecules to sufficient conditions to denature GC-poor regions but not to denature GC-rich regions, thereby producing GC-rich regions suitable for amplification; and subjecting the plurality to amplification conditions such that the denatured GC-poor regions are substantially not amplified and such that one or more of the non-denatured or partially denatured GC-rich regions are amplified.

In specific embodiments, the conditions to denature GC-poor regions but not to denature GC-rich regions comprise temperature sufficient to denature GC-poor regions but not to denature GC-rich regions, pressure sufficient to denature GC-poor regions but not to denature GC-rich regions, pH sufficient to denature GC-poor regions but not to denature GC-rich regions, or a combination thereof. In further specific embodiments, the conditions to denature GC-poor regions but not to denature GC-rich regions comprise temperature sufficient to denature GC-poor regions but not to denature GC-rich regions.

In certain aspects of the invention, the subjecting the plurality of DNA molecules to sufficient conditions to denature GC-poor regions but not to denature GC-rich regions is further defined as: subjecting the plurality to a first temperature such that the GC-poor regions are substantially denatured and such that the GC-rich regions are undenatured or are denatured only in part; and subjecting the plurality to a second temperature such that at least part of the GC-poor regions incompletely renature and such that at least part of the GC-rich regions substantially completely renature, thereby producing renatured amplifiable GC-rich molecules.

In specific embodiments, the molecules comprising GC-rich regions are further defined as comprising one or more regions having GC content greater than about 50%. In further specific embodiments, the first temperature is greater than about 60° C. and/or the second temperature is lower than about 85° C.

Methods of the invention may further comprise ligating an adaptor onto the end of at least some of the renatured GC-rich molecules to produce adaptor-ligated molecules. In a specific embodiment, the ends of the renatured GC-rich molecules are polished prior to said ligating, and in particular aspects the ligating is further defined as blunt-end ligating. In additional aspects, the renatured GC-rich molecules are further defined as restriction enzyme fragments, and wherein the adaptors are suitable for ligation onto the respective digested fragment ends. The ligating may be further defined as ligating with both strands of the DNA molecules and the adaptors. The ligating may be further defined as ligating with only one strand of each molecule, said one strand being the 5' end of the DNA molecules and the 3' end of the adaptors, wherein the method further comprises 3' extension of a nick in the adaptor-ligated molecules.

In specific embodiments, the GC-poor regions that are substantially denatured are further defined as having one or more regions that are single stranded following said subjecting step, and wherein the single stranded regions are subjected to a single strand-specific endonuclease, such as one that comprises S1 nuclease, P1 nuclease, Mung bean nuclease, or a mixture thereof. The method may further comprise subjecting the adaptor-ligated DNA molecules to one or more methylation-sensitive restriction enzymes. In additional embodiments, the method further comprises subjecting the adaptor-ligated DNA molecules to one or more methylation-specific restriction enzymes.

In particular aspects, an adaptor of the invention is further defined as a stem-loop oligonucleotide comprising an inverted repeat and a loop. The adaptor may be further defined as comprising a restriction endonuclease site. The endonuclease site may be present in the inverted repeat, for example. In certain aspects, the methods of the invention further comprise subjecting the adaptor-ligated molecules to the restriction endonuclease.

The DNA molecule that is provided may be from a body fluid or tissue, and a body fluid may comprise blood, serum, urine, cerebrospinal fluid, nipple aspirate, sweat, or saliva. In specific embodiments, the tissue comprises biopsy, surgical sample, or cheek scrapings.

Amplification for the invention may comprise polymerase chain reaction. In additional specific embodiments, the plurality of DNA molecules comprise known sequences at the ends of the molecules. Methods of the invention may further comprise determining at least part of the sequence of one or more of the amplified molecules. In specific aspects, the determined sequence comprises a regulatory sequence. In specific embodiments, the determining step provides diagnostic information for an individual, and the diagnostic information may comprise cancer diagnosis information for the individual. In a specific embodiment, the GC-rich region comprises at least part of regulatory sequence, such as at least part of a CpG island.

In another embodiment, there is a method of amplifying a CpG island from a molecule, comprising: providing a plurality of DNA molecules, said plurality comprising at least one molecule having at least one CpG island and said plurality having at least one molecule comprising one or more regions that are GC-poor; subjecting the plurality of DNA molecules to sufficient conditions to denature GC-poor regions but not to substantially denature the CpG island, thereby rendering the CpG island suitable for amplification; and subjecting the plurality to amplification conditions such that the denatured GC-poor regions are substantially not amplified and such that the non-denatured or partially denatured CpG island is amplified. In a specific embodiment, the CpG island is further defined comprising at least part of a regulatory sequence.

In an additional embodiment of the invention, there is a method of preparing a library, comprising: providing a plurality of DNA molecules, said plurality having molecules comprising one or more regions that are GC-poor and having molecules comprising one or more regions that are GC-rich; subjecting the plurality of DNA molecules to sufficient conditions to denature GC-poor regions but not to denature GC-rich regions, thereby producing GC-rich regions suitable for amplification; and subjecting the plurality to amplification conditions such that the denatured GC-poor regions are substantially not amplified and such that one or more of the non-denatured or partially denatured GC-rich regions are amplified. In specific embodiments, the method further comprises ligating an adaptor onto the end of at least some of the renatured GC-rich molecules to produce adaptor-ligated molecules, and in certain aspects the ends of the renatured GC-rich molecules are polished prior to said ligating, which may be further defined as blunt-end ligating. In specific embodiments, the renatured GC-rich molecules are further defined as restriction enzyme fragments, and wherein the adaptors are suitable for ligation onto the respective digested fragment ends.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features that are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawing, in which:

FIG. 9 shows a one-step, one-tube preparation process for synthesis of DNA molecules with inverted repeat at the ends.

DETAILED DESCRIPTION OF THE INVENTION

Figure 1:
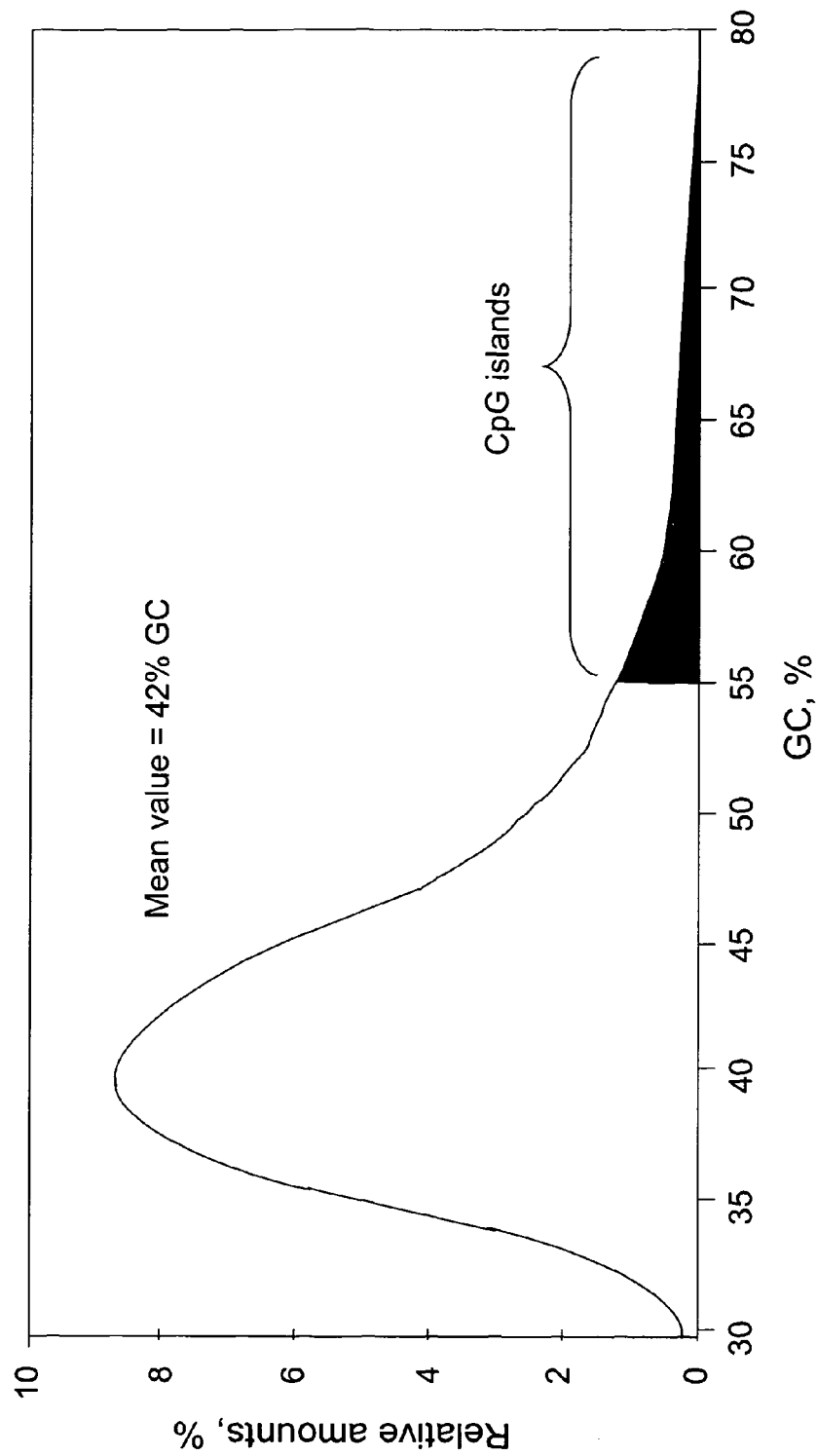
FIG. 1 shows GC distribution of total human DNA based on CsCl absorbance density gradient profile and human genome sequence analysis, with a mean value at 42% GC. The distribution has very little DNA above 55% GC, however this DNA fraction has much higher gene density and contains a majority of CpG islands and GC-rich promoters (shown in black).

The present application incorporates by reference herein in its entirety U.S. patent application Ser. No. 11/071,864, filed Mar. 3, 2005. Also incorporated by reference herein in its entirety is U.S. Patent Application Ser. No. 11/366,222, filed Mar. 2, 2006, entitled "Compositions and Methods for Processing and Amplification of DNA, including Using Multiple Enzymes in a Single Reaction,"which itself claims priority to U.S. Provisional Patent Application Ser. No. 60/704,932, filed Aug. 2, 2005.

I. Definitions

In keeping with long-standing patent law convention, the words "a" and "an" when used in the present specification in concert with the word comprising, including the claims, denote "one or more." Some embodiments of the invention may consist of or consist essentially of one or more elements, method steps, and/or methods of the invention. It is contemplated that any method or composition described herein can be implemented with respect to any other method or composition described herein.

The practice of the present invention will employ, unless otherwise indicated, conventional techniques of molecular biology, microbiology, recombinant DNA, and so forth which are within the skill of the art. Such techniques are explained fully in the literature. See e.g., Sambrook, Fritsch, and Maniatis, MOLECULAR CLONING: A LABORATORY MANUAL, Second Edition (1989), OLIGONUCLEOTIDE SYNTHESIS (M. J. Gait Ed., 1984), ANIMAL CELL CULTURE (R. I. Freshney, Ed., 1987), the series METHODS IN ENZYMOLOGY (Academic Press, Inc.); GENE TRANSFER VECTORS FOR MAMMALIAN CELLS (J. M. Miller and M. P. Calos eds. 1987), HANDBOOK OF EXPERIMENTAL IMMUNOLOGY, (D. M. Weir and C. C. Blackwell, Eds.), CURRENT PROTOCOLS IN MOLECULAR BIOLOGY (F. M. Ausubel, R. Brent, R. E. Kingston, D. D. Moore, J. G. Siedman, J. A. Smith, and K. Struhl, eds., 1987), CURRENT PROTOCOLS IN IMMUNOLOGY (J. E. Coligan, A. M. Kruisbeek, D. H. Margulies, E. M. Shevach and W. Strober, eds., 1991); ANNUAL REVIEW OF IMMUNOLOGY; as well as monographs in journals such as ADVANCES IN IMMLNOLOGY. All patents, patent applications, and publications mentioned herein, both supra and infra, are hereby incorporated herein by reference.

A skilled artisan recognizes that there is a conventional single letter code in the art to represent a selection of nucleotides for a particular nucleotide site. For example, R refers to A or G; Y refers to C or T; M refers to A or C; K refers to G or T; S refers to C or G; W refers to A or T; H refers to A or C or T; B refers to C or G or T; V refers to A or C or G; D refers to A or G or T; and N refers to A or C or G or T.

The term "blunt end" as used herein refers to the end of a dsDNA molecule having 5' and 3' ends, wherein the 5' and 3' ends terminate at the same nucleotide position. Thus, the blunt end comprises no 5' or 3' overhang.

The term "CpG island" as used herein is defined as an area of DNA that is enriched in CG dinucleotide sequences (cytosine and guanine nucleotide bases) compared to the average distribution within the genome. The generally accepted CpG island constitutes a region of at least 200-bp of DNA with a G+C content of at least 50% and observed CpG/expected CpG ratio of least 0.6. In specific aspects, the CpG island has GC content of about 55% to about 80%. In further embodiments, the CpG island comprises about 60% GC to about 70% GC. In certain aspects, moderately GC-rich CpG islands may be considered 50-60% GC, and this group represents about 30% of all CpG islands; GC-rich CpG islands may be considered 60-70% GC, and this group represents about 60% of all CpG islands; and extremely GC-rich CpG islands may be considered greater than about 70% GC, and this group represents about 10% of all CpG islands.

The term "double stranded molecule" as used herein refers to a molecule that is double stranded at least in part.

The term "GC-poor" as used herein refers to DNA molecules with the G+C content less than 50%. In particular aspects, the GC-poor DNA comprises about 30% GC to about 50% GC, and in additional aspects the GC-poor DNA comprises less than about 45% GC, less than about 40% GC, less than about 35% GC, less than about 30% GC, less than about 25% GC, and so forth.

The term "GC-rich" as used herein refers to DNA molecules with the G+C content more than 50%. In particular aspects, the GC-rich DNA comprises about 60% GC to about 70% GC, and in additional aspects, the GC-rich DNA comprises greater than about 55% GC, greater than about 60% GC, greater than about 65% GC, greater than about 70% GC, greater than about 75% GC, greater than about 80% GC, and so forth.

The terms "hairpin" and "stem-loop oligonucleotide" as used herein refer to a structure formed by an oligonucleotide comprised of 5' and 3' terminal regions that are inverted repeats and a non-self-complementary central region, wherein the self-complementary inverted repeats form a double-stranded stem and the non-self-complementary central region forms a single-stranded loop.

The term "methylation-sensitive restriction endonuclease" as used herein refers to a restriction endonuclease that is unable to cut DNA that has at least one methylated cytosine present in the recognition site. A skilled artisan recognizes that the term "restriction endonuclease" may be used interchangeably in the art with the term "restriction enzyme."

The term "methylation-specific restriction endonuclease" as used herein regards an enzyme that cleaves DNA comprising at least one methylcytosine on at least one strand. In a specific embodiment, the McrBC enzyme is utilized and will not cleave unmethylated DNA. A skilled artisan recognizes that the term "restriction endonuclease" may be used interchangeably in the art with the term "restriction enzyme."

The term "Methylome" as used herein is defined as the collective set of genomic fragments comprising methylated cytosines, or alternatively, a set of genomic fragments that comprise methylated cytosines in the original template DNA.

The term "polished" as used herein refers to the repair of a dsDNA fragment termini that may be enzymatically repaired, wherein the repair constitutes the fill in of recessed 3' ends or the exonuclease activity trimming back of 5' ends to form a "blunt end" compatible with adaptor ligation.

The term "substantially completely renature" as used herein refers to the majority of GC-rich regions being renatured. In specific aspects, the term refers to greater than 50%, greater than about 55%, greater than about 60%, greater than about 65%, greater than about 70%, greater than about 75%, greater than about 80%, greater than about 85%, greater than about 90%, greater than about 95%, or greater than about 97% of GC-rich regions being renatured.

The term "substantially denatured" as used herein refers to the majority of GC-poor regions being denatured. In specific aspects, the term refers to greater than 50%, greater than about 55%, greater than about 60%, greater than about 65%, greater than about 70%, greater than about 75%, greater than about 80%, greater than about 85%, greater than about 90%, greater than about 95%, or greater than about 97% of GC-poor regions being denatured.

The term "substantially not amplified" as used herein refers to the majority of denatured GC-poor regions not being amplified. In specific aspects, the term refers to greater than 50%, greater than about 55%, greater than about 60%, greater than about 65%, greater than about 70%, greater than about 75%, greater than about 80%, greater than about 85%, greater than about 90%, greater than about 95%, or greater than about 97% of GC-poor regions not being amplified.

II. Specific Embodiments of the Invention

Figure 3:
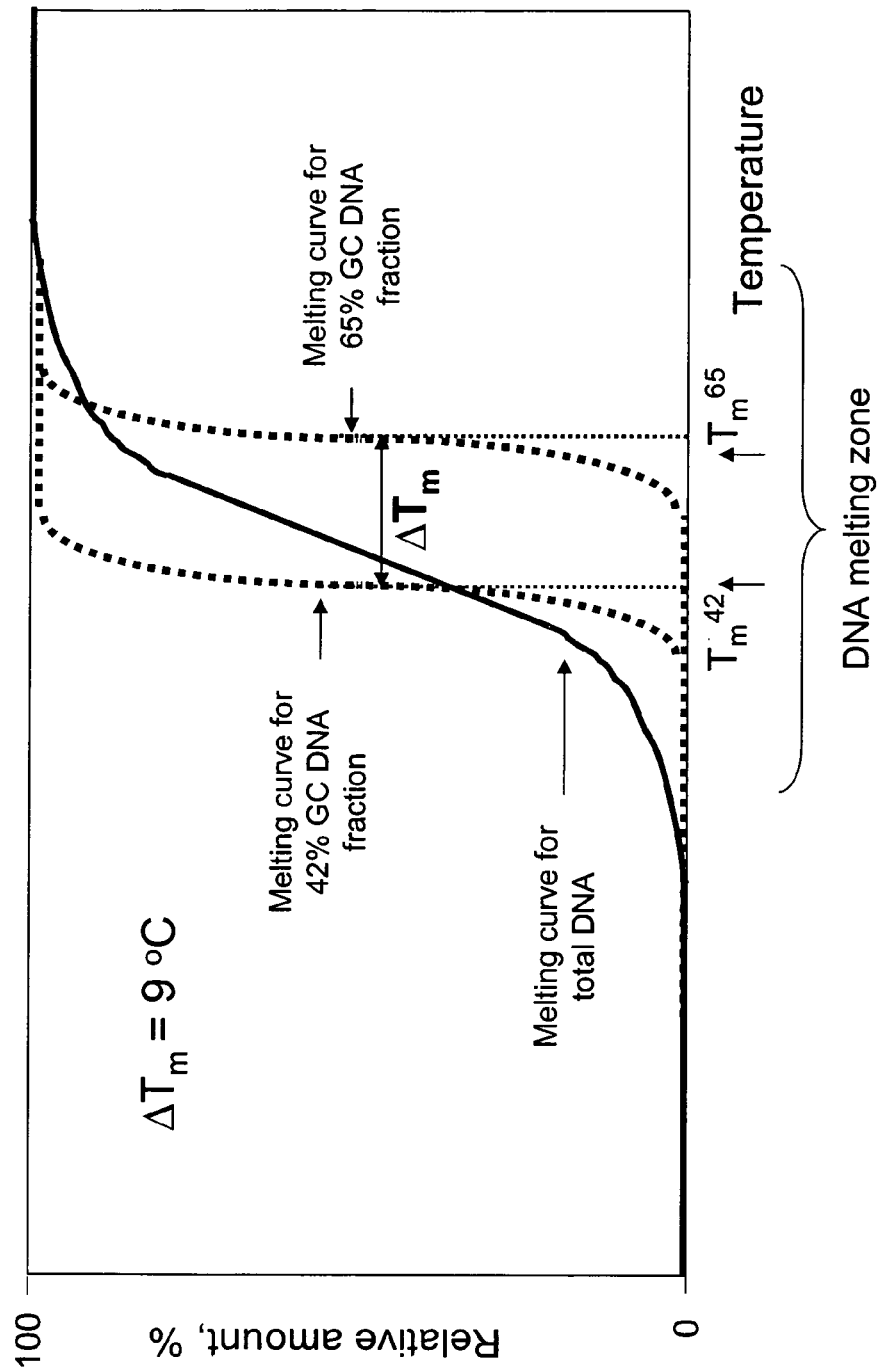
FIG. 3 shows DNA melting profiles for total human DNA (broad melting zone) and two hypothetical DNA fractions with 42% and 65% GC content and corresponding melting temperatures $T_m^{42}$ and $T_m^{65}$ (narrow melting zones). Calculated difference $\Delta T_m = T_m^{65} - T_m^{42}$ in the melting temperature for these two fractions is about 9° C.

A. Basic Principles of CpG Island DNA Isolation by Thermal Segregation and Enzymatic Selection Approach In this embodiment of the invention, there is a general description of the principle of the CpG island isolation (enrichment). It is known that double-stranded DNA fragments undergo strand dissociation when they are exposed to denaturing conditions, such as heat; alkaline or acidic conditions with non-physiological pH; or organic solvents. DNA fragments with higher G+C content exhibit higher stability towards denaturing agents and melt at a higher temperature than fragments with low G+C composition. When fragmented genomic DNA that is characterized by a wide GC distribution is exposed to heat (see FIG. 1), it melts within a broad rather than narrow temperature zone, as opposed to DNA fractions with more homogeneous GC composition (FIG. 3). DNA melting temperature ($T_m$) depends on many parameters that include G+C content, DNA fragment length, ionic strength of the buffer, etc. The effects of these factors can be approximated by a simple equation: $T_m=81+16.6(\log_{10}C)+0.4$ [% GC]$-600/N$, where C is the salt concentration and N is the length of the DNA fragment in base pairs. The expected difference in melting temperature for two DNA fragments #1 and #2 (fractions) with equal size (size distribution) and buffer conditions is entirely determined by the difference in their G+C content, namely $\Delta T_m=0.4\{$[% GC]$_2-$[% GC]$_1\}$. For example, for DNA molecules with 42% and 65% GC content, the difference in $T_m$ is 9.2° C.

Figure 2:
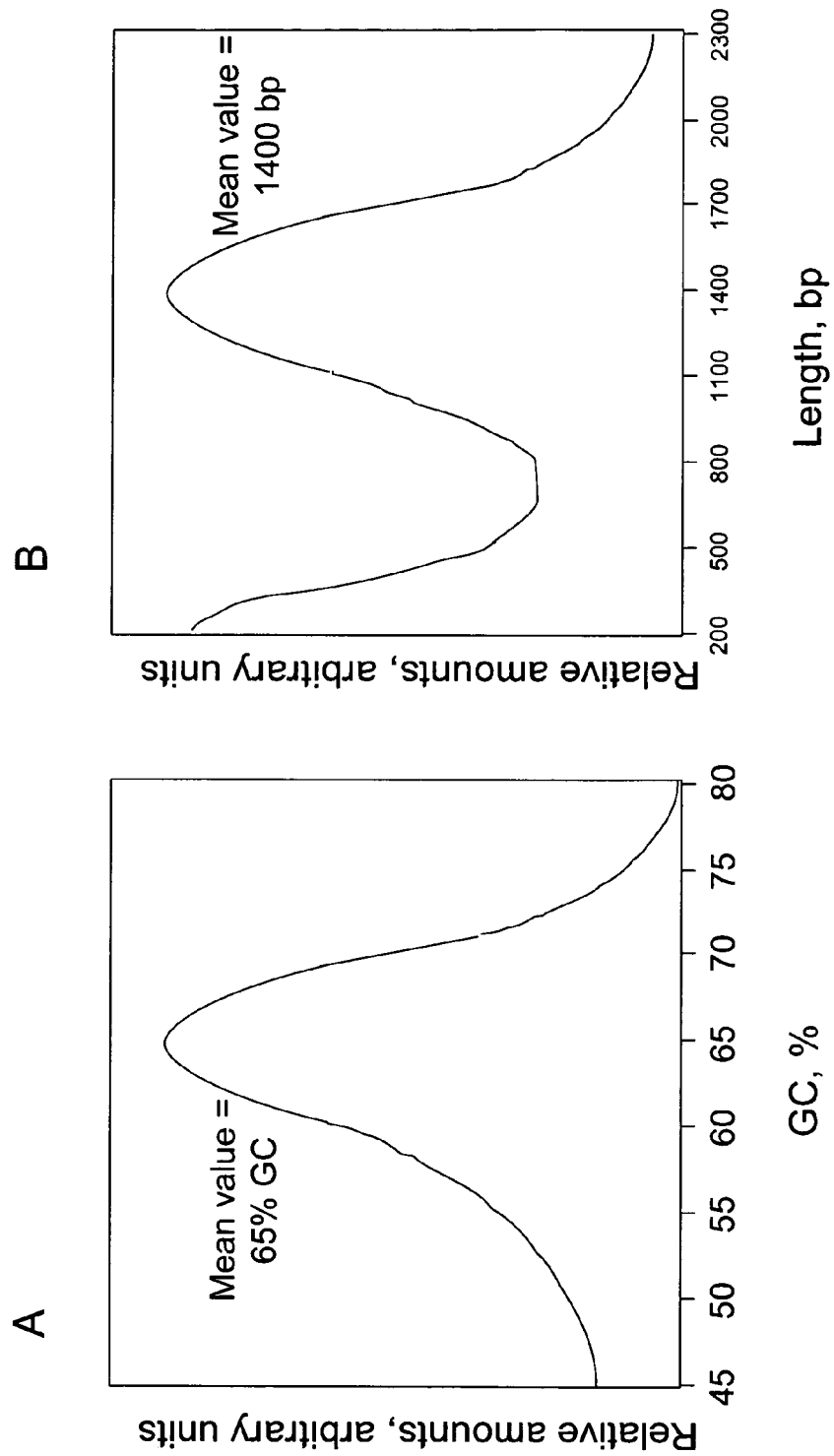
FIG. 2A shows GC distribution of the CpG islands associated with the 5' regions of genes in exemplary human chromosomes 21 and 22, with a mean value at ~65% GC.
FIG. 2B shows length distribution of the CpG islands associated with the 5' regions of genes in exemplary human chromosomes 21 and 22, with an average length of 1400 bp.

FIG. 1 and FIG. 2A show G+C distribution of total DNA and the CpG islands associated with the 5' regions of genes, respectively. These islands constitute only 1-2% of total DNA (FIG. 1), have an average size about 1.4 kb (FIG. 2B), and GC content about 65% (FIG. 2A) which is 23% higher than the average GC content of genomic DNA (FIG. 1). It is expected that the major human CpG island fraction characterized by the average GC content of 65% (FIG. 2A) will have almost 10° C. higher melting temperature than the average genomic DNA with the GC content of 42% (FIG. 1).

Figure 4:
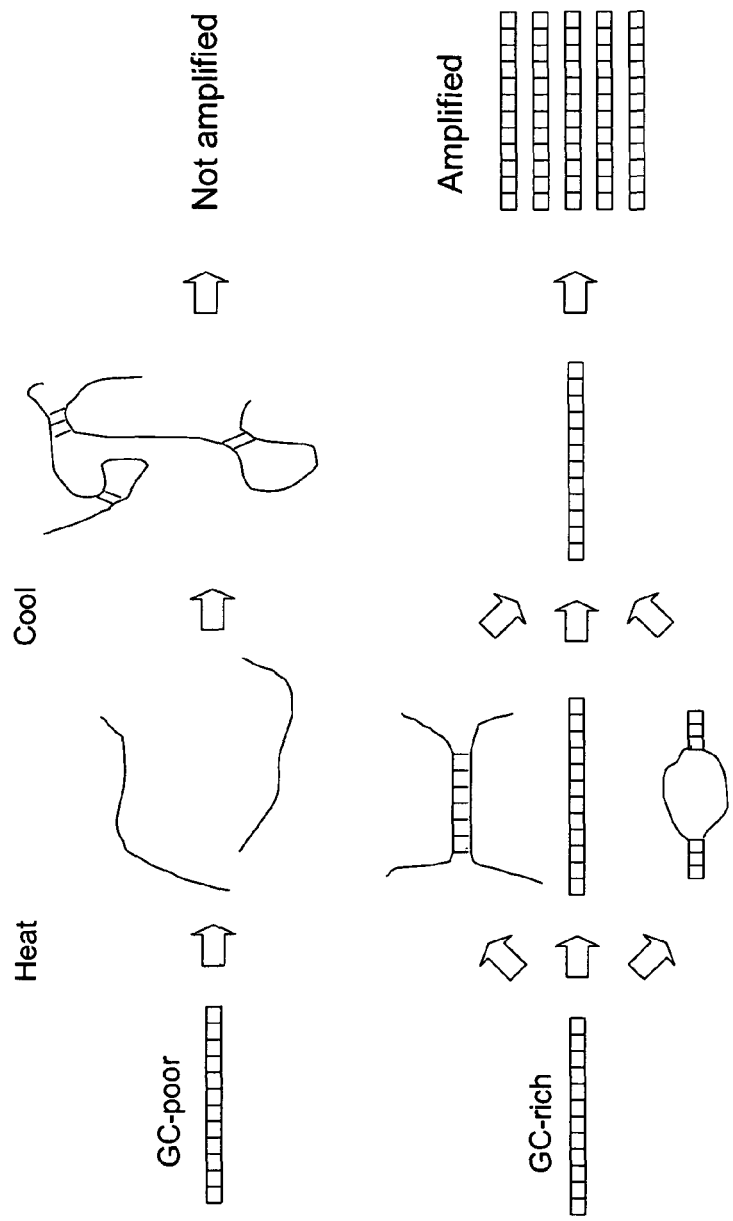
FIG. 4 is a general description of the thermal segregation and enzymatic selection-amplification method used for isolation of the GC-rich DNA fraction.

When a mixture of double-stranded DNA fragments with a heterogeneous base composition and size range form about 50 bp to about 3,000 bp is exposed to the appropriate heat-denaturing conditions (temperature and salt concentration) the majority of GC-poor DNA fragments (for example, <55% GC) can be denatured and converted into a single-stranded form. The small GC-rich DNA fraction (>55% GC) will still possess a double-stranded or partially double-stranded conformation (FIG. 4). After cooling down to a lower temperature (for example, about 37° C.), the GC-poor DNA fraction will remain in a single-stranded conformation (unique, low copy DNAs) or form partial duplexes (repetitive, high copy DNAs), while the GC-rich DNA fraction will retain its original double-stranded structure.

The GC-rich double-stranded DNA fraction segregated from the GC-poor DNA by the above-described heating process can be selectively processed into a DNA library by one or more enzymatic reactions and amplified (FIG. 4). The GC-poor single-stranded DNA would be not efficiently processed into a library, and as a result is present in the amplified material at a significantly reduced concentration.

Segregation of DNA fragments into GC-poor and GC-rich fractions can be also achieved by DNA exposure to other denaturing conditions such as high or low pH (Cantor and Schimmel), chaotropic reagents, elevated or reduced pressure (Dubnis D. N., et al., (2001), or a combination thereof.

B. CpG Island DNA Isolation Using Selection-By-Ligation Method

Figure 5:
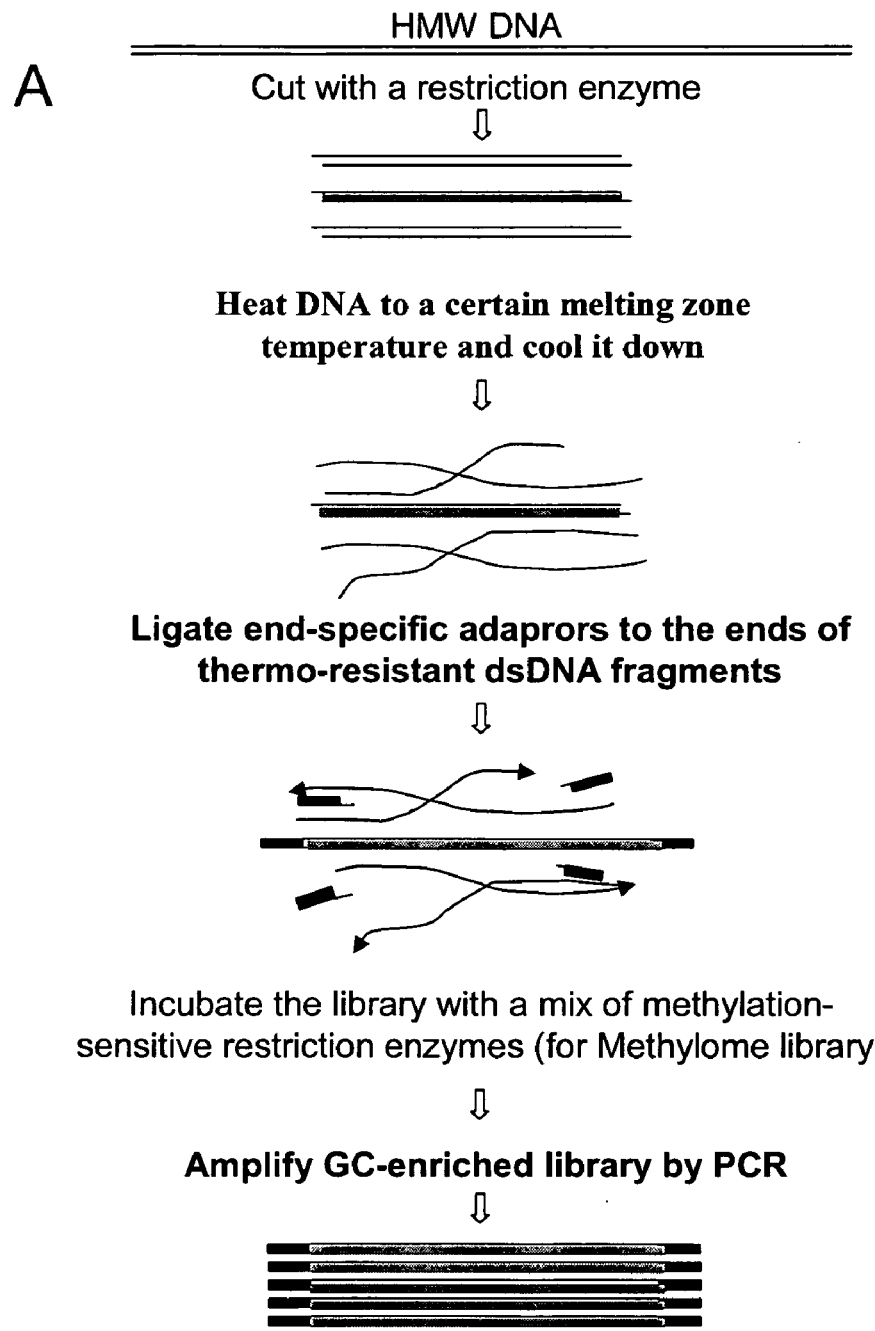
FIGS. 5A-5D illustrate the selection-by-ligation approach wherein DNA molecules produced by restriction digestion of HMW DNA (FIGS. 5A and 5C) or endogenously cleaved (for example, from serum or urine) and polished DNA fragments (FIGS. 5B and 5D) are exposed to a partially-denaturing temperature and then ligated with an oligonucleotide adaptor. Only GC-rich molecules that retain double-stranded structure and template affinity for the adaptor ligation reaction are converted into a library and amplified during PCR.
Figure 5:
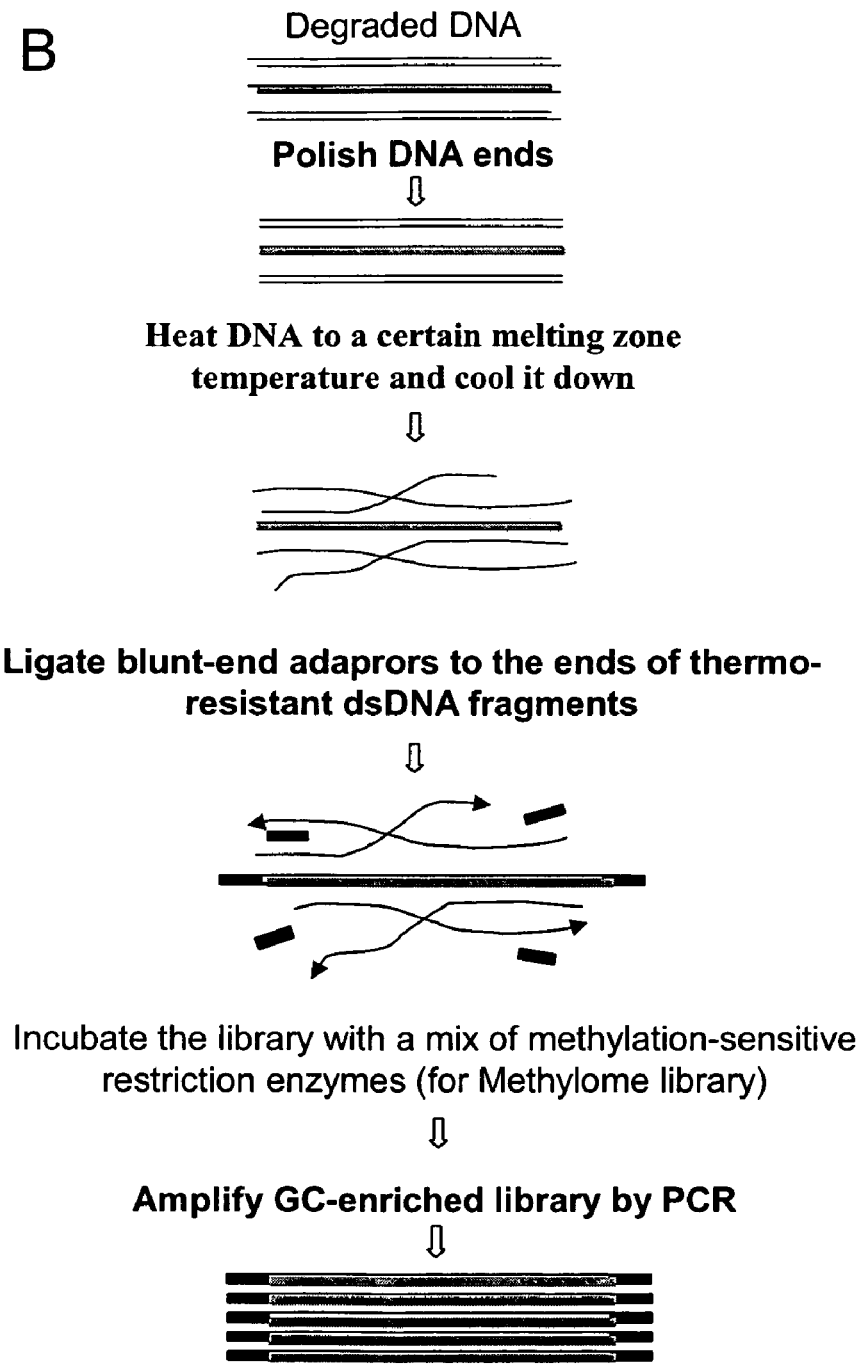
Figure 5:
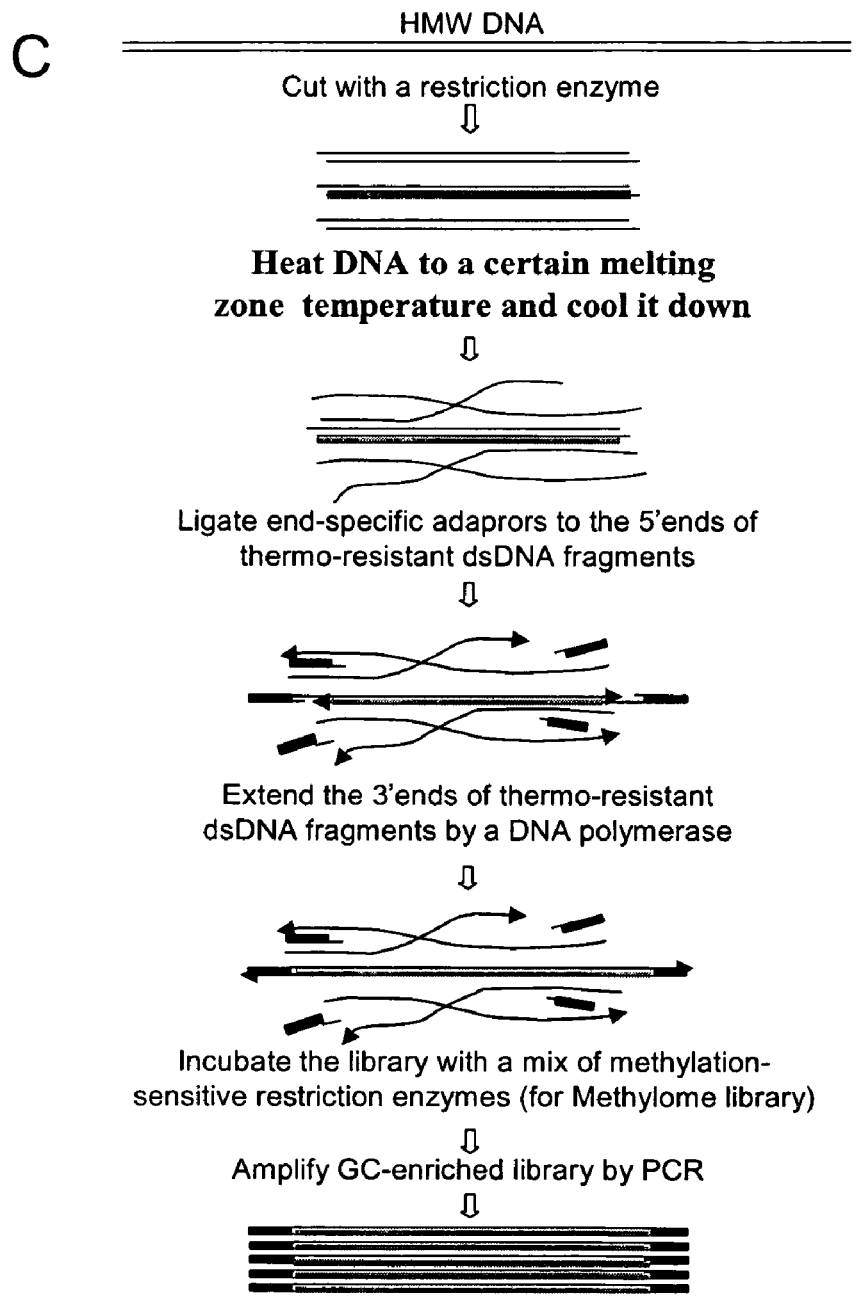
Figure 5:
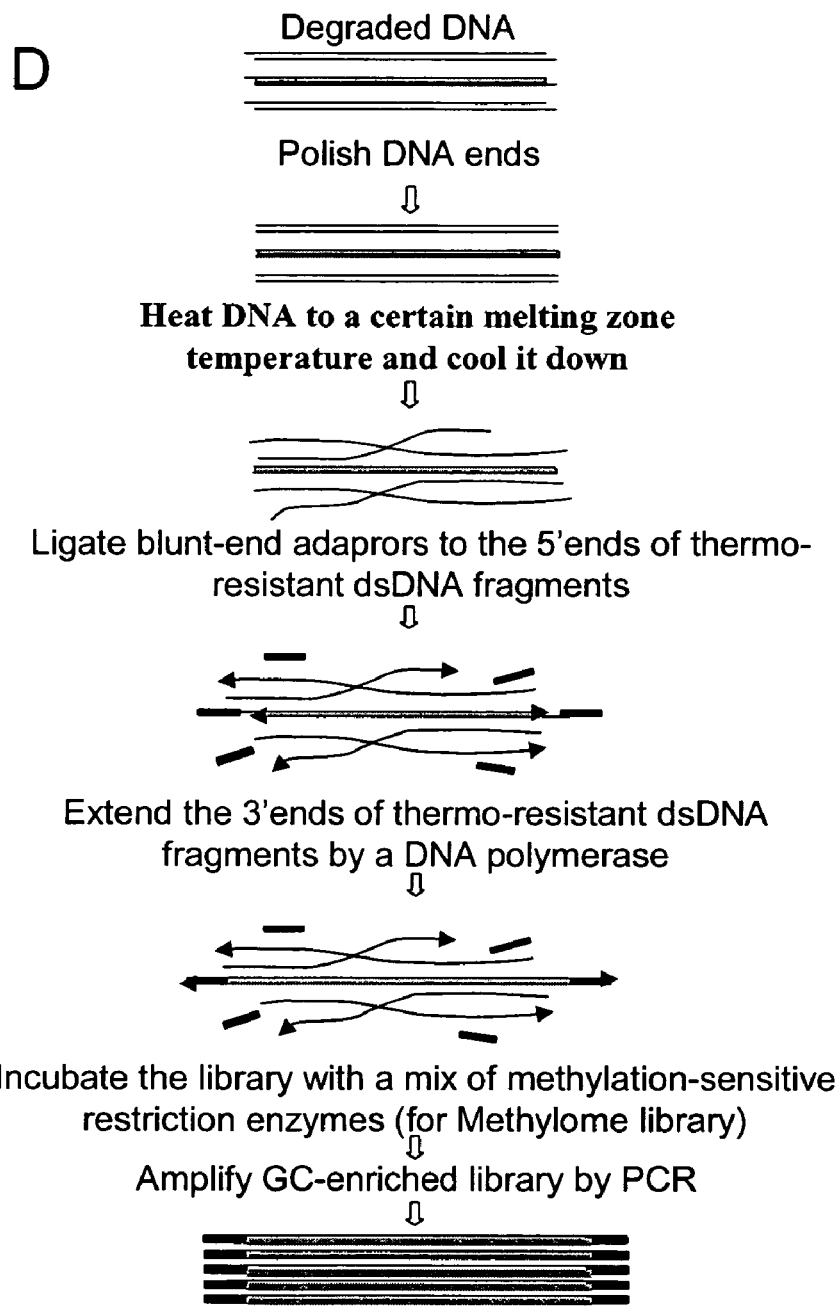

In this embodiment of the present invention, as illustrated in FIG. 5, there is a description of the CpG island isolation method that uses a specific enzymatic step in the DNA library preparation and amplification as a tool to select and isolate double-stranded DNA molecules that survive a heat-denaturing process. Specifically, the method described in FIG. 5 uses the adaptor ligation reaction to select double-stranded molecules.

The method utilizes adaptors that have only one ligation-competent end. One type of adaptor has both 3' and 5' termini participating in the ligation process. In this case, the adaptor has the 3' hydroxyl and the 5' phosphate groups at one end and neither the 5' phosphate group nor the 3' hydroxyl group at another end. A second type of adaptors has only one 3' terminus participating in the ligation reaction. In this case, the adaptor has the 3' and 5' hydroxyl groups at one end and neither the 5' phosphate group nor the 3' hydroxyl group at another end. The ligation-competent end of the adaptor can be blunt or has a 3' or 5' protruding termini complementary to the ends of DNA restriction fragments.

DNA used in the selection process can be intact and have high molecular weight (HMW) (FIGS. 5A and 5C), or it can be degraded (cell-free DNA from blood or urine, DNA extracted from FFPE tissues, etc.) and have size from about 100 bp to about 2-3 kb (FIGS. 5B and 5D).

In one embodiment of the invention, prior to heating DNA is polished with a proofreading DNA polymerase to generate blunt DNA ends (FIG. 5B and 5D). In this case, adaptors participating in the ligation-selection reaction after DNA heating also have one blunt end that is competent for ligation. In one specific embodiment, the adaptor has a ligation-competent 3' end with the hydroxyl group and a ligation-competent 5' end with the phosphate group (FIG. 5B). In this case, the ligation reaction selects all GC-rich double-stranded DNA molecules and converts them into a library of DNA fragments that can be directly amplified by PCR (FIG. 5B).

Specifically, DNA is (1) incubated with a proofreading DNA polymerase (such as Klenow fragment of the DNA polymerase I (exo+), T4 DNA polymerase, T7 DNA polymerase, etc.) to generate blunt ends; (2) heated at a certain temperature for about 5-15 min to denature most GC-poor DNA fragments and then cooled down; (3) incubated with blunt-end oligonucleotide adaptors with the 3' hydroxyl and 5' phosphate groups, and T4 DNA ligase; and (4) generated whole genome (WGA) library is amplified by PCR (FIG. 5B).

In a specific embodiment, when the goal is to create a GC-enriched Whole Methylome DNA library, the product of ligation reaction (WGA library) is incubated with a mix of methylation-sensitive restriction enzymes such as Aci I, Acc II, Asp LE I, Ava I, Bce AI, Bsa HI, Bsh 1236 I, Bsi E1, Bsi SI, Bst FN I, Bst HH I, Bst UI, Cfo I, Hap II, Hga I, Hha I, HinP1 I, Hin 6I, Hpa II, Hpy 99I, Hpy CH4 IV, Hsp AI, Mvn I, and Ssi, for example (FIG. 5B), or with methylation-specific enzymes such as McrBC nuclease, for example.

In another specific embodiment, an adaptor has a ligation-competent 3' end with a hydroxyl group and ligation-resistant 5' end (FIG. 5D). In this case, the ligation reaction links the adaptor to only one DNA strand, specifically to the 5' end, leaving a nick between the 3' end of DNA and the 5' end of adaptor. To complete the library synthesis, the 3' end of DNA is then extended by a DNA polymerase towards the adaptor end (FIG. 5D). Selected by ligation and converted into a library as described above, GC-rich DNA fragments can be amplified by PCR (FIG. 5D).

Specifically, DNA is (1) incubated with a proofreading DNA polymerase (such as Klenow fragment of the DNA polymerase I (exo+), T4 DNA polymerase, T7 DNA polymerase, etc) to create blunt ends, (2) heated at a certain temperature for about 5-15 min to denature most GC-poor DNA fragments and then cooled down; (3) incubated with blunt-end oligonucleotide adaptors with the 3' and 5' hydroxyl groups, and T4 DNA ligase; (4) incubated with a DNA polymerase to extend the 3' DNA end into the adaptor region; and (5) created whole genome (WGA) library is amplified by PCR (FIG. 5D).

In a specific embodiment, when the goal is to generate a GC-enriched Whole Methylome DNA library, the product of polymerase-extension reaction (WGA library) is incubated with a mix of methylation-sensitive restriction enzymes such as Aci I, Acc II, Asp LE I, Ava I, Bce AI, Bsa HI, Bsh 1236 I, Bsi E1, Bsi SI, Bst FN I, Bst HH I, Bst UI, Cfo I, Hap II, Hga I, Hha I, HinP1 I, Hin 61I, Hpa II, Hpy 99I, Hpy CH4 IV, Hsp AI, Mvn I, and Ssi, for example (FIG. 5D), or with methylation-specific enzymes such as McrBC nuclease, for example.

In another embodiment of the invention, prior to heating DNA is digested with a restriction enzyme to generate DNA termini with 5' protruding, 3' protruding, or blunt ends (FIGS. 5A and 5C). In this case, adaptors participating in the ligation-selection reaction after DNA heating also have one compatible 5' protruding, 3' protruding, or blunt end that is competent for ligation. In one specific embodiment, an adaptor has a ligation-competent 3' end with the hydroxyl group and a ligation-competent 5' end with the phosphate group (FIG. 5A). In this case, the ligation reaction selects all GC-rich, double-stranded DNA molecules and converts them into a library of DNA fragments that can be directly amplified by PCR (FIG. 5A).

Specifically, HMW DNA is (1) digested with a restriction endonuclease; (2) heated at a certain temperature for about 5-15 min to denature most GC-poor DNA fragments and then cooled down; (3) incubated with oligonucleotide adaptors that have one compatible 5' protruding, 3' protruding, or blunt end with the 3' hydroxyl and the 5' phosphate groups, and a DNA ligase; and (4) the generated whole genome (WGA) library is amplified by PCR (FIG. 5A).

In a specific embodiment, when the goal is to generate a GC-enriched Whole Methylome DNA library, the product of ligation reaction (WGA library) is incubated with a mix of methylation-sensitive restriction enzymes such as Aci I, Acc II, Asp LE I, Ava I, Bce AI, Bsa HI, Bsh 1236 I, Bsi E1, Bsi SI, Bst FN I, Bst HH I, Bst UI, Cfo I, Hap II, Hga I, Hha I, HinP1 I, Hin 6I, Hpa II, Hpy 99I, Hpy CH4 IV, Hsp AI, Mvn I, and Ssi, for example (FIG. 5A), or with methylation-specific enzymes such as McrBC nuclease, for example.

In another specific embodiment, an adaptor has a ligation-competent 3' end with a hydroxyl group and ligation-resistant 5' (FIG. 5C). In this case, the ligation reaction links the adaptor to only one DNA strand, specifically to the 5' end, leaving a nick between the 3' end of DNA and the 5' end of adaptor. To complete the library synthesis the 3' end of DNA is then extended by a DNA polymerase towards the adaptor end (FIG. 5C). Selected by ligation and converted into a library as described above, GC-rich DNA fragments can be amplified by PCR (FIG. 5C).

Specifically, HMW DNA is (1) digested with a restriction endonuclease; (2) heated at a certain temperature for about 5-15 min to denature most GC-poor DNA fragments and then cooled down; (3) incubated with oligonucleotide adaptors that have one compatible 5' protruding, 3' protruding, or blunt end with the 3' and 5' hydroxyl groups, and a DNA ligase; (4) incubated with a DNA polymerase to extend the 3' DNA end into the adaptor region; and (5) the generated whole genome (WGA) library is amplified by PCR (FIG. 5C).

In a specific embodiment, when the goal is to generate a GC-enriched Whole Methylome DNA library, the product of ligation reaction (WGA library) is incubated with a mix of methylation-sensitive restriction enzymes such as Aci I, Acc II, Asp LE I, Ava I, Bce AI, Bsa HI, Bsh 1236 I, Bsi E1, Bsi SI, Bst FN I, Bst HH I, Bst UI, Cfo I, Hap II, Hga I, Hha I, HinP1 I, Hin 6I, Hpa II, Hpy 99I, Hpy CH4 IV, Hsp AI, Mvn I, and Ssi, for example (FIG. 5C), or with methylation-specific enzymes such as McrBC nuclease, for example.

C. CpG Island DNA Isolation Using Selection-By-Polymerization Method

Figure 6:
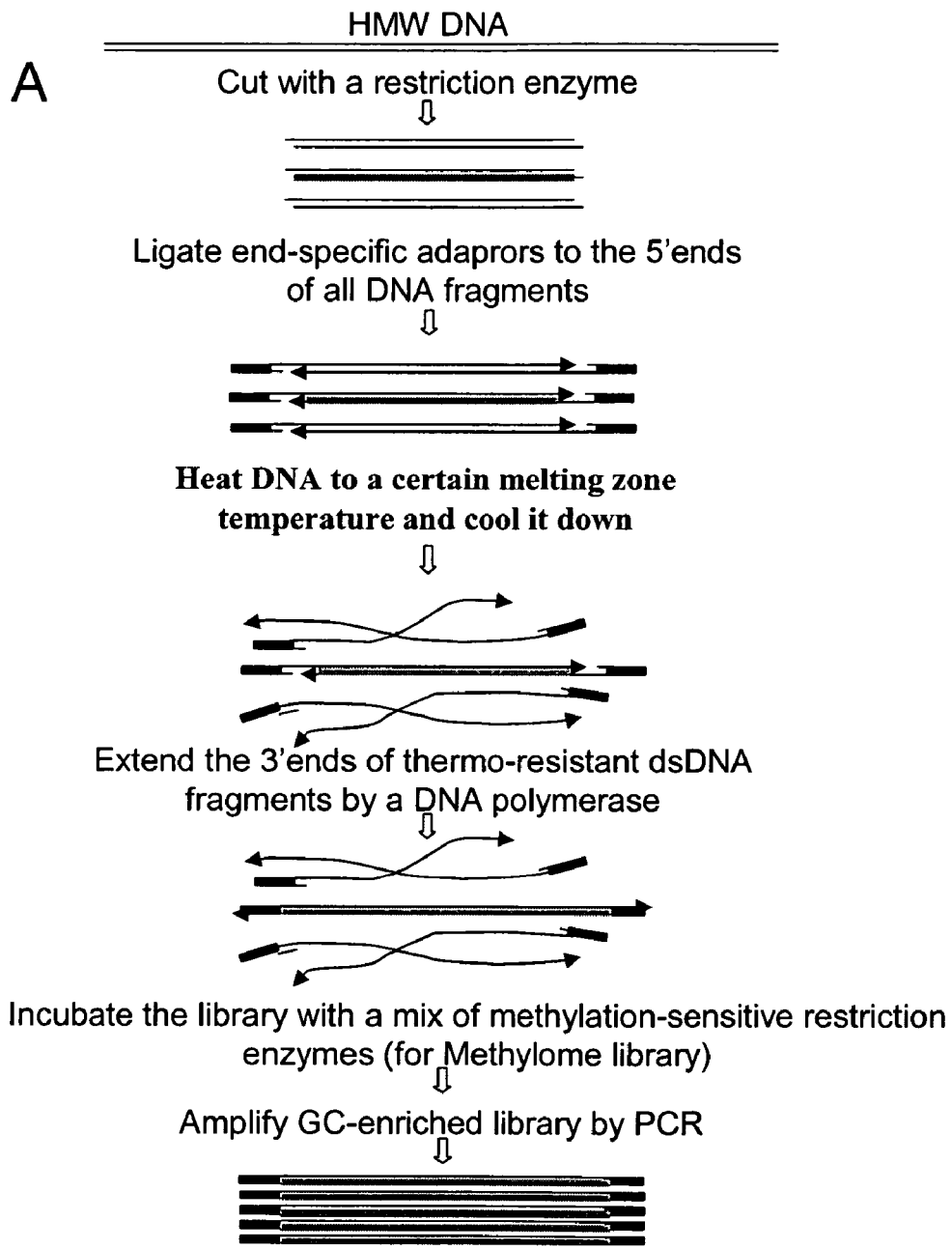
FIGS. 6A-6B illustrate the selection-by-extension approach where DNA molecules produced by restriction digestion of HMW DNA (FIG. 6 or endogenously cleaved (for example, from serum or urine) and polished DNA fragments (FIG. 6B) are ligated with an oligonucleotide adaptor and then exposed to a partly-denaturing temperature prior to the 3' end extension reaction. Only GC-rich molecules that retain double-stranded structure and template capacity for the 3' extension reaction are converted into a library and amplified during PCR.
Figure 6:
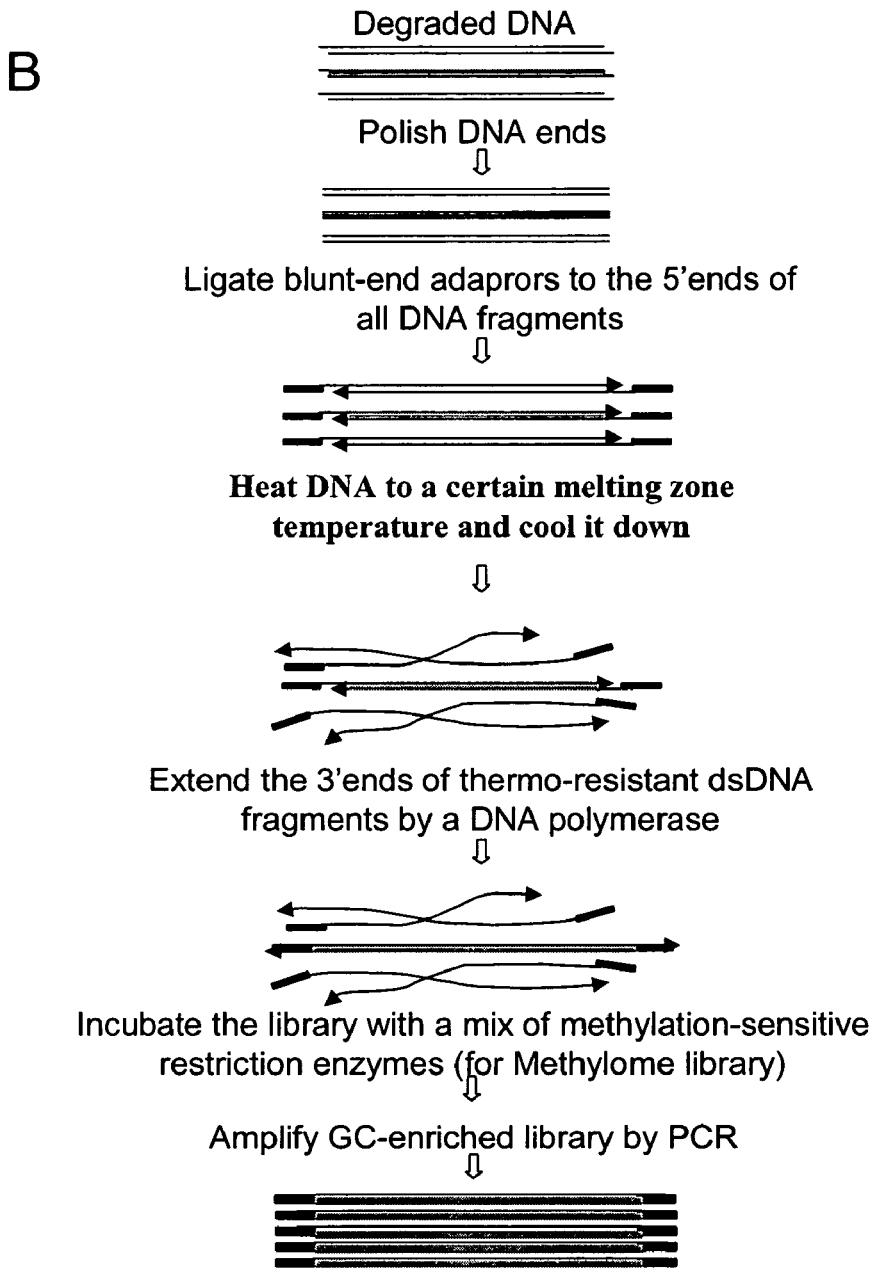

In this embodiment of the present invention, as illustrated in FIG. 6, there is a description of the CpG island isolation method that uses a specific enzymatic step in the DNA library preparation and amplification as a tool to select and isolate double-stranded DNA molecules that survive a heat-denaturing process. Specifically, the method described in FIG. 6 uses the 3' end DNA extension-polymerization reaction to select double-stranded molecules.

The method utilizes adaptors that have only one ligation-competent end, specifically the 3' end with a hydroxyl group. The adjacent 5' end has a hydroxyl group that is ligation-resistant. This adaptor end can be blunt, or has a 3' or 5' protruding ter-mini complementary to the ends of DNA restriction fragments. The opposite end of the adaptor has neither the 5' phosphate group nor the 3' hydroxyl group.

DNA used in the selection process can be intact and have high molecular weight (HMW) (FIG. 6A), or it can be degraded (such as from cell-free DNA from blood, urine, or DNA extracted from FFPE tissues, for example) and have size from about 100 bp to about 2-3 kb (FIG. 6B).

In one embodiment of the invention, prior to adaptor ligation DNA is polished with a proofreading DNA polymerase to generate blunt DNA ends (FIG. 6B). In this case, adaptors participating in the ligation-selection reaction after DNA heating also have the blunt end that is competent for ligation.

Specifically, DNA is (1) incubated with a proofreading DNA polymerase (such as Klenow fragment of the DNA polymerase I (exo+), T4 DNA polymerase, T7 DNA polymerase, etc.) to generate blunt ends; (2) incubated with blunt-end oligonucleotide adaptors with the 3' and 5' hydroxyl groups, and a DNA ligase (such as T4 DNA ligase); (3) heated at a certain temperature for about 5-15 min to denature most GC-poor DNA fragments and then cooled down; (4) incubated with a DNA polymerase to extend the 3' DNA end into the adaptor region in molecules that survive the heat treatment and retain a double-stranded conformation; and (5) the generated whole genome (WGA) library is amplified by PCR (FIG. 6B).

In a specific embodiment, when the goal is to generate a GC-enriched Whole Methylome DNA library, the product of polymerase-extension reaction (WGA library) is incubated with a mix of methylation-sensitive restriction enzymes such as Aci I, Acc II, Asp LE I, Ava I, Bce AI, Bsa HI, Bsh 1236 I, Bsi E1, Bsi SI, Bst FN I, Bst HH I, Bst UI, Cfo I, Hap II, Hga I, Hha I, HinP 1I, Hin 6I, Hpa II, Hpy 99I, Hpy CH4 IV, Hsp AI, Mvn I, and Ssi, for example (FIG. 6B), or with methylation-specific enzymes such as McrBC nuclease, for example.

In another embodiment of the invention, prior to adaptor ligation DNA is digested with a restriction enzyme to generate DNA termini with 5' protruding, 3' protruding or blunt ends (FIG. 6A). In this case, adaptors participating in the ligation-selection reaction after DNA heating also have one compatible 5' protruding, 3' protruding, or blunt end that is competent for ligation.

Specifically, DNA is (1) digested with a restriction endonuclease; (2) incubated with oligonucleotide adaptors that have one compatible 5' protruding, 3' protruding, or blunt end with the 3' and 5' hydroxyl groups, and a DNA ligase; (3) heated at a certain temperature for about 5-15 min to denature most GC-poor DNA fragments and then cooled down; (4) incubated with a DNA polymerase to extend the 3' DNA end into the adaptor region in molecules that survive the heat treatment and retain a double-stranded conformation; and (5) the generated whole genome (WGA) library is amplified by PCR (FIG. 6A).

In a specific embodiment, when the goal is to generate a GC-enriched Whole Methylome DNA library, the product of polymerase-extension reaction (WGA library) is incubated with a mix of methylation-sensitive restriction enzymes such as Aci I, Acc II, Asp LE I, Ava I, Bce AI, Bsa HI, Bsh 1236 I, Bsi E1, Bsi SI, Bst FN I, Bst HH I, Bst UI, Cfo I, Hap II, Hga I, Hha I, HinP1 I, Hin 6I, Hpa II, Hpy 99I, Hpy CH4 IV, Hsp AI, Mvn I, and Ssi, for example (FIG. 6A), or with methylation-specific enzymes such as McrBC nuclease, for example.

D. CpG Island DNA Isolation Using Selection-By-Degradation Method

Figure 7:
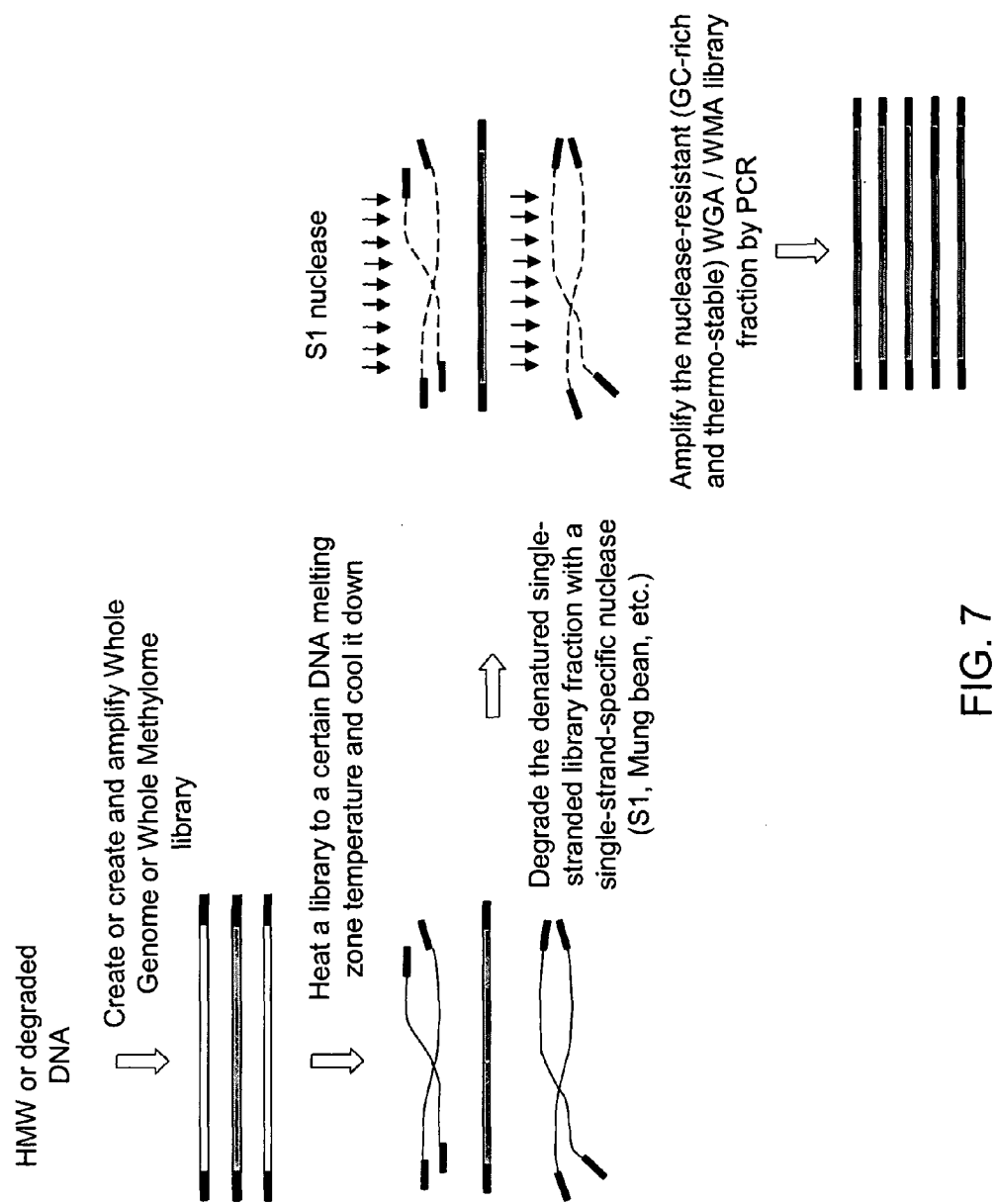
FIG. 7 is a description of the thermo-enrichment method for selection and amplification of the GC-rich DNA fraction that utilizes the selection-by-degradation approach where DNA converted to a library form (and amplified if necessary) is exposed to a partly-denaturing temperature and then incubated with a single strand-specific nuclease to destroy GC-poor amplicons. Only GC-rich molecules that retain double-stranded structure and resistance to a single-strand specific nuclease are amplified during PCR.

In this embodiment of the present invention, as illustrated in FIG. 7, there is a description of the CpG island isolation method that uses a specific enzymatic step that is implemented after DNA library preparation but prior to its amplification or even after library amplification as a tool to select and isolate double-stranded DNA molecules that survive a heat-denaturing process. Specifically, the method described in FIG. 7 uses single-stranded DNA degradation by structure-specific nucleases, such as S1 or Mung bean nuclease, for example, to select and amplify GC-rich double-stranded DNA molecules that survive heat treatment.

DNA used in the selection process can be intact and have high molecular weight (HMW), or it can be degraded (such as cell-free DNA from blood, urine, or DNA extracted from FFPE tissues, for example) and have size from about 100 bp to about 2-3 kb.

The DNA library, Whole Genome Library or Whole Methylome Library can be synthesized using any method described herein, or presented in other patent applications (see, for example, U.S. patent application Ser. No. 11/071, 864 and U.S. Provisional Patent Application Ser. No. 60/704, 932, filed Aug. 2, 2005 and entitled, COMPOSITIONS AND METHODS FOR PROCESSING AND AMPLIFICATION OF DNA, INCLUDING USING MULTIPLE ENZYMES IN A SINGLE REACTION, by inventors Vladimir L. Makarov, Emmanuel Kamberov, and Brendan Tarrier, both of which are incorporated by reference herein in their entirety). The selection process can be implemented before or after library amplification. Selected DNA fragments should be amplified or re-amplified to increase the concentration of GC-rich DNA molecules, in specific embodiments.

The process of DNA selection involves (1) DNA fragmentation (if necessary) and whole genome (WGA) or whole Methylome (WMA) library synthesis; (2) library heating to a certain temperature for about 5-15 min to denature most GC-poor DNA amplicons and then cooling; (3) incubation with a single-strand specific nuclease (such as, for example, S1, P1, Mung bean, etc.); and (4) buffer replacement and amplification of the nuclease-resistant GC-rich fraction by PCR.

It should be noted that universal sequences introduced to both ends of DNA molecules during library synthesis should have low or moderate GC-content (<50% GC) to prevent formation of stable GC-clamps at DNA termini that could affect efficiency of DNA segregation by melting process.

E. CpG Island DNA Isolation Using Selection-By-Inactivation Method

Figure 10:
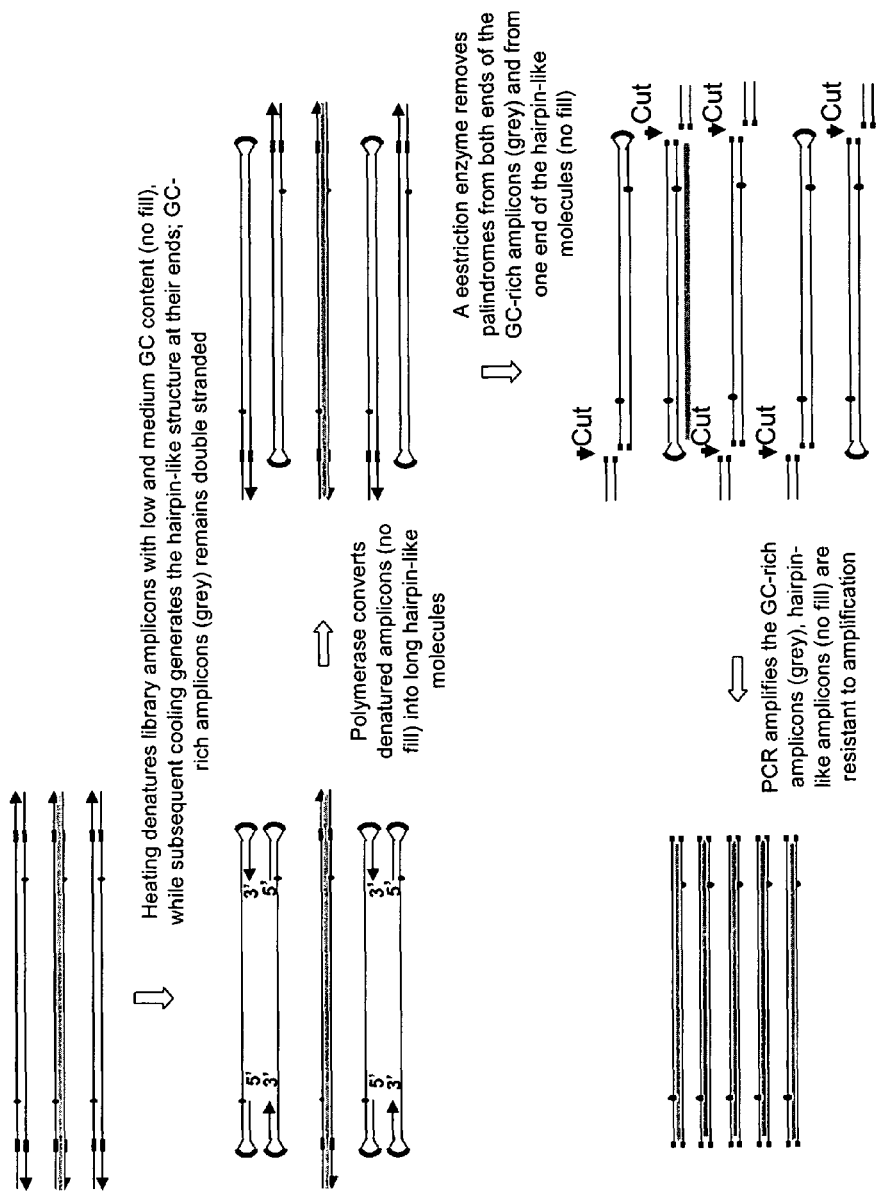
FIG. 10 is a description of the thermo-enrichment method for selection and amplification of the GC-rich DNA fraction that utilizes the selection-by-inactivation approach where a DNA library with inverted repeat adaptors is exposed to a partially-denaturing temperature and then incubated with a DNA polymerase and a restriction nuclease that cuts adaptors and eliminates palindromes from the ends of GC-rich amplicons. Only the GC-rich fragments that remain double-stranded and do not form terminal hairpins are converted into amplifiable molecules by restriction digestion and subsequently amplified by PCR.

In this embodiment of the present invention, as illustrated in FIG. 10, there is a description of the CpG island isolation method that uses a special DNA library adaptor design and specific enzymatic steps that are implemented during DNA library preparation as a tool to select and isolate double-stranded DNA molecules that survive a heat-denaturing process. Specifically, the method described in FIG. 10 uses DNA molecules with inverted repeats and a restriction site at the ends (FIG. 8) that are introduced by a one-step enzymatic process (shown in FIG. 9. and described in detail in patent application entitled, "COMPOSITIONS AND METHODS FOR PROCESSING AND AMPLIFICATION OF DNA, INCLUDING USING MULTIPLE ENZYMES IN A SINGLE REACTION," filed concomitantly herewith by inventors Vladimir L. Makarov, Emmanuel Kamberov, and Brendan Tarrier, which is incorporated by reference herein in their entirety). It is an intermediate product during DNA library synthesis for inactivation of all GC-poor DNA molecules, but selection and amplification of the GC-rich double-stranded DNA fraction that survives a heat treatment and an inactivation process.

Figure 8:
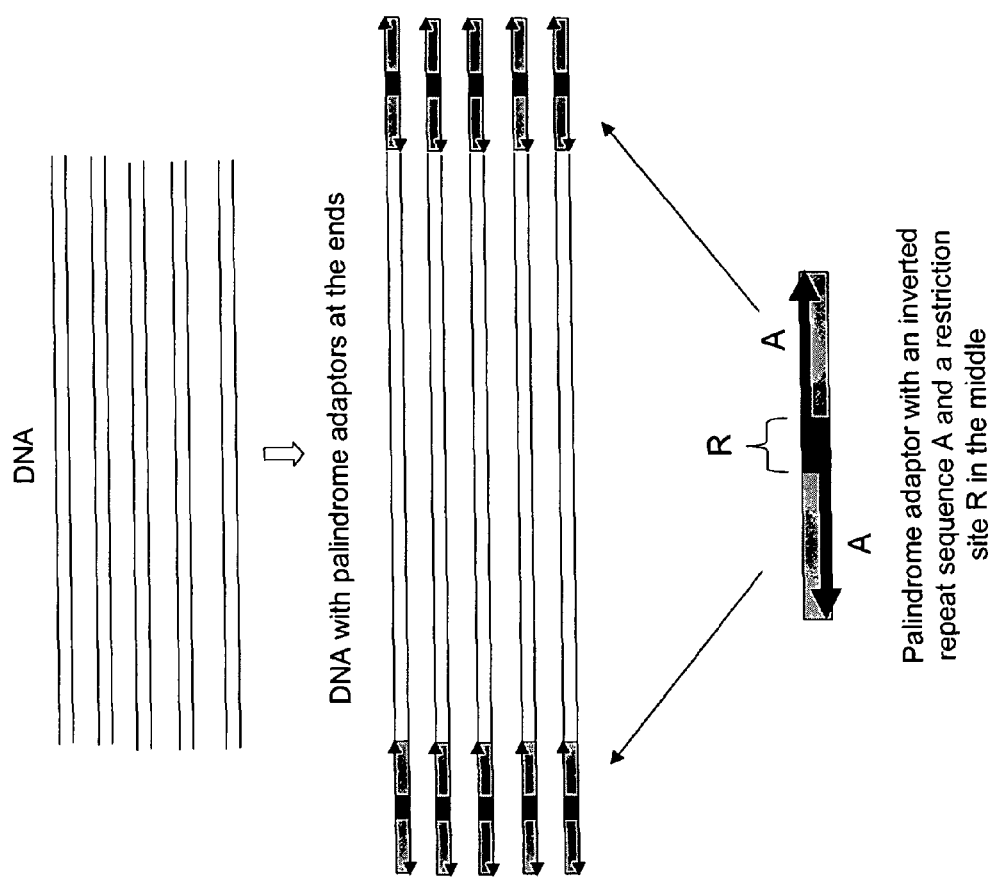
FIG. 8 shows a DNA library with inverted repeat adaptors.

In a specific embodiment, as shown in FIG. 9, DNA molecules with inverted repeats and a restriction site within a repeat are prepared by incubation of fragmented DNA (which in further specific embodiments is naturally degraded, such as from cell-free blood or urine DNA, or DNA produced by a nuclease digestion, for example) with a mixture comprising the following: 1) a stem-loop oligonucleotide with the following: a) 3' recessed, 3' protruding, or a blunt end and a 5' hydroxyl group (FIG. 10); b) a specific DNA sequence S comprising a loop or contained within the loop; and c) an adjacent stem region; 2) an endonuclease that cleaves a restriction site R when the oligonucleotide adopts a double-stranded conformation; 3) a 3' proofreading DNA polymerase (Klenow fragment of the DNA polymerase I or T4 DNA polymerase, for example) 4) a DNA ligase; 5) Universal Buffer; 6) ATP; and 7) dNTPs. Three enzymatic reactions are taking place in the same multi-step process: "polishing" of the DNA ends and the stem-loop oligonucleotide double-stranded stem-region; ligation of the oligonucleotide 3' end to the 5' phosphate of the DNA leaving a nick between the 3' end of DNA and the 5' end of the hairpin double-stranded stem-region; and polymerase extension of the 3' DNA end that propagates toward the end of stem-loop oligonucleotide and generates inverted repeats at the ends of DNA fragments and forms cleavable restriction sites R in the middle of the palindromes instead of non-cleavable sites S within the stem-loop oligonucleotides. The process results in DNA molecules with inverted repeats and restriction sites within a repeat at the ends of DNA fragments (FIGS. 8 and 9).

In another specific embodiment, as illustrated in FIG. 10, there is a selection process that involves the following: (1) preparation of DNA molecules with inverted repeats and a restriction site within a repeat (as shown in FIG. 9); (2) heating DNA molecules at a temperature that denatures GC-poor amplicons with a subsequent cooling; (3) incubation with a DNA polymerase that converts denatured fragments into long stem-loop molecules that are resistant to PCR amplification; (4) incubation with a restriction endonuclease R that removes palindromes from both ends of heat-resistant GC-rich molecules and converts them into an amplifiable DNA library (restriction cleavage at one end of the long hairpin DNA molecules does not generate amplifiable molecules); and (5) amplification of the selected GC-rich DNA fraction by PCR. In some embodiments steps (3) and (4) can be combined into one by incubation of intermediate DNA molecules with inverted repeats with a mixture of DNA polymerase and a restriction enzyme.

In a specific embodiment, when the goal is to generate a GC-enriched Whole Methylome DNA library, the intermediate product of the one-step enzymatic reaction (DNA molecules with inverted repeats) (FIGS. 8 and 9) is incubated with a mix of methylation-sensitive restriction enzymes such as Aci I, Acc II, Asp LE I, Ava I, Bce AI, Bsa HI, Bsh 1236 I, Bsi E1, Bsi SI, Bst FN I, Bst HH I, Bst UI, Cfo I, Hap II, Hga I, Hha I, HinP1 I, Hin 6I, Hpa II, Hpy 99I, Hpy CH4 IV, Hsp AI, Mvn I, and Ssi, for example, or with methylation-specific enzymes such as McrBC nuclease, for example, prior to the selection process described in FIG. 10. In this case, the nuclease digestion can be carried out concomitantly in combination with other enzymatic reactions that produce molecules with inverted repeats (see above discussion, FIG. 9, and U.S. patent application Ser. No. 11/071,864, filed Mar. 3, 2005, and a patent application filed concurrently herewith and entitled "COMPOSITIONS AND METHODS FOR PROCESSING AND AMPLIFICATION OF DNA, INCLUDING USING MULTIPLE ENZYMES IN A SINGLE REACTION," by inventors Vladimir L. Makarov, Emmanuel Kamberov, and Brendan Tarrier, both of which are incorporated by reference herein in their entirety). Digestion with methylation-sensitive or methylation-specific nucleases can be also performed after or during a selection step that involves incubation with a DNA polymerase and restriction digestion within the inverted repeat site R.

F. Application of the CpG Island-Enriched Methylome Libraries for Marker Discovery and Molecular Diagnostics of Cancer In this embodiment, Methylome library synthesis described in the patent application U.S. patent application Ser. No. 11/071,864, filed Mar. 3, 2005, employs methods for additional enrichment of CpG-rich genomic DNA from substantially fragmented DNA.

Methylome libraries as described therein are very powerful tools that permit the analysis of DNA methylation from very limited sample amounts, such as substantially fragmented samples including, for example, cell-free DNA recovered from blood and/or urine; DNA isolated from biopsies; and DNA isolated from formalin fixed paraffin embedded tissues. When combined with real-time PCR analysis, as few as 2 or 3 methylated DNA molecules can be detected in a blood or urine sample, for example. This level of robustness and sensitivity presents opportunities for multiple non-invasive diagnostic applications of the methods of U.S. patent application Ser. No. 11/071,864, filed Mar. 3, 2005. Methylome libraries are characterized by a high degree of complexity, and the analysis of global methylation patterns may best be resolved by hybridization to high resolution DNA microarrays, for example. To maximize the specificity and sensitivity of Methylome analysis, an efficient enrichment method may be employed to increase the relative copy number of CpG-rich DNA within the Methylome library.

Previously, the present inventors described an enrichment method that applied secondary Methylome libraries and demonstrated that there was a 16-128-fold enrichment level for the various exemplary methylated promoter regions (U.S. patent application Ser. No. 11/071,864, filed Mar. 3, 2005). Secondary Methylome libraries demonstrate an increased efficiency in identifying methylated CpG regions; however, the complex synthesis process may limit their application. Here the present invention provides an alternative approach of Methylome library enrichment for the CpG-rich genomic regions that is easier and faster than the secondary Methylome library method, specifically, the thermo-enrichment method.

In one specific embodiment, as described generally in Section B and FIG. 5C, and in detail in Example 1 and FIG. 11, aliquots of blunt-end DNA fragments produced by Alu I digestion of human DNA were pre-heated for 10 min in 1× NEBuffer 4 at 75° C. (control), 83° C., 84.1° C., 85.3° C., 87° C., 89.1° C., 91.4° C., 93.5° C., 94.9° C., 96° C., or snap-cooled on ice, and incubated with T4 DNA ligase, $K_U$ adaptor and ATP. After completion of the fill-in synthesis at the recessed 3' ends (15 min at 75° C.), whole genome libraries were amplified and then quantitatively analyzed using real-time PCR and primer pairs for different promoter regions. It was found that pre-heating DNA at temperatures between 89° C. and 94° C. resulted in 4 to 128-fold (median about 60-fold) enrichment of the amplified WGA library for all tested promoter regions.

In another specific embodiment, described generally in Section B and FIG. 5D, and in detail in Example 2 and FIG. 12, aliquots of cell-free DNA isolated from urine and "polished" by Klenow fragment of DNA polymerase I underwent thermo-enrichment for 10 min in 1× NEBuffer 4 at 75° C. (control), 89° C., 91° C., or 93° C., were snap-cooled on ice, and we incubated with T4 DNA ligase, $K_U$ adaptor, and ATP. Libraries were subsequently digested with a cocktail of methylation-sensitive restriction enzymes Aci I, HhaI, Hpa II, HinP1 I, and Bst UI, filled-in to replicate the sequence of the non-ligated adaptor strand, and amplified by PCR. Real-time PCR analysis of two CpG islands within the amplified libraries revealed a significant enrichment for the thermo-enriched Methylome libraries with a maximum enrichment level for these promoters observed in libraries prepared with pre-heating at 89° C. and 91° C.

A skilled artisan recognizes that all above-described methods of selection for the GC-rich double-stranded DNA fraction after pre-heating step can be used for Methylome library enrichment. Thermo-enrichment of GC-rich DNA is a simple and rapid method for increasing the sensitivity and specificity of Methylome libraries. When used in combination with the One-step Methylome library synthesis, it can easily be implemented for high through-put methylation analysis of clinical DNA samples for cancer diagnostics, and in many other research and medical areas. CpG-enriched Methylome libraries prepared by the thermal segregation and enzymatic selection-amplification method may be used as the method of choice for preparing libraries for genome-wide methylation analysis.

Application of the CpG island-enriched genomic libraries for gene discovery.

As CpG islands often overlap transcription units, CpG-rich DNA libraries prepared by the thermal segregation and enzymatic selection-amplification method can be used to isolate full-length cDNAs for associated genes and promoter sequences in human and other vertebrates.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

EXAMPLES

The following examples are included to demonstrate preferred embodiments of the invention. It should be appreciated by those of skill in the art that the techniques disclosed in the examples which follow present techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Enrichment of Libraries Prepared From ALUI Digested Genomic DNA for Promoter Sequences by Heat Treatment This example demonstrates that genomic libraries prepared from AluI-digested DNA essentially as described in U.S. patent application Ser. No. 10/797,333, filed Mar. 8, 2004, now abandoned, can be enriched for promoter sequences by pre-heating fragmented DNA prior to library preparation at temperatures that will selectively denature subsets of DNA fragments based on their GC content, thus making part of the genome incompetent for ligation.

Human genomic DNA isolated from the peripheral blood of a healthy donor by standard procedures was digested with 10 units of AluI restriction endonuclease (NEB) for 1 hour following the manufacturer's protocol. Aliquots of 70 ng were pre-heated in 15 μl of 1× NEBuffer 4 (NEB) for 10 min at 75° C. (control), 83° C., 84.1° C., 85.3° C., 87° C., 93.5° C., 94.9° C., 96° C., or 97° C. followed by snap-cooling at −10° C. in an ice/ethanol bath.

For library preparation, the pre-heated DNA samples were incubated in a reaction mixture comprising 1× NEBuffer 4, 1.25 μM of universal $K_U$ adaptor (Table I), 800 units of T4 DNA ligase, and 1 mM ATP in a final volume of 21 μ. Ligation was carried out for 1 hour at 25° C. followed by 15 min at 75° C.

Libraries were amplified by quantitative PCR by supplementing the reactions with PCR master mix adding to the following final concentrations: 1 × Titanium Taq reaction buffer (Clontech), 200 μM of each dNTP, fluorescein calibration dye (1:100,000) and SYBR Green I (1:100,000), 1 μM universal primer $K_U$ (Table I, SEQ ID NO: 15), 4% DMSO, 200 μM 7-deaza-dGTP (Sigma), and 5 units of Titanium Taq polymerase (Clontech) in a final volume of 75 μ. After initial incubation at 75° C. for 15 min to fill-in the recessed 3' ends of the ligated DNA libraries, amplifications were carried out at 95° C. for 3 min, followed by cycling at 94° C. for 15 sec and 65° C. for 2 min on an I-Cycler real-time PCR instrument (Bio-Rad). Amplified libraries were purified using Multi-Screen PCR cleanup system (Millipore) and quantified by optical density reading.

Forty nanograms of purified library DNA were used to analyze promoter sequences of high, intermediate, or low GC content by quantitative PCR as exemplified by the GSTP-1, MDR-1, and APC promoters, respectively. Quantitative PCR was performed in reaction mixtures comprising the following: 1× Titanium Taq reaction buffer (Clontech), 200 μM of each dNTP, 4% DMSO, 0.5 M betaine, FCD (1:100,000) and SYBR Green I (1:100,000), 200 nM each forward and reverse primer (Table II, SEQ ID NO:13 and SEQ ID NO:14 for GSTP-1 promoter, SEQ ID NO:5 and SEQ ID NO:6 for APC-1 promoter, and SEQ ID NO:7 and SEQ ID NO:8 for MDR-1 promoter), and 1.5 units of Titanium Taq polymerase (Clontech) in a final volume of 15 μl at 95° C. for 3 min followed by 50 cycles at 94° C. for 15 sec and 68° C. for 1 min.

Figure 11A:
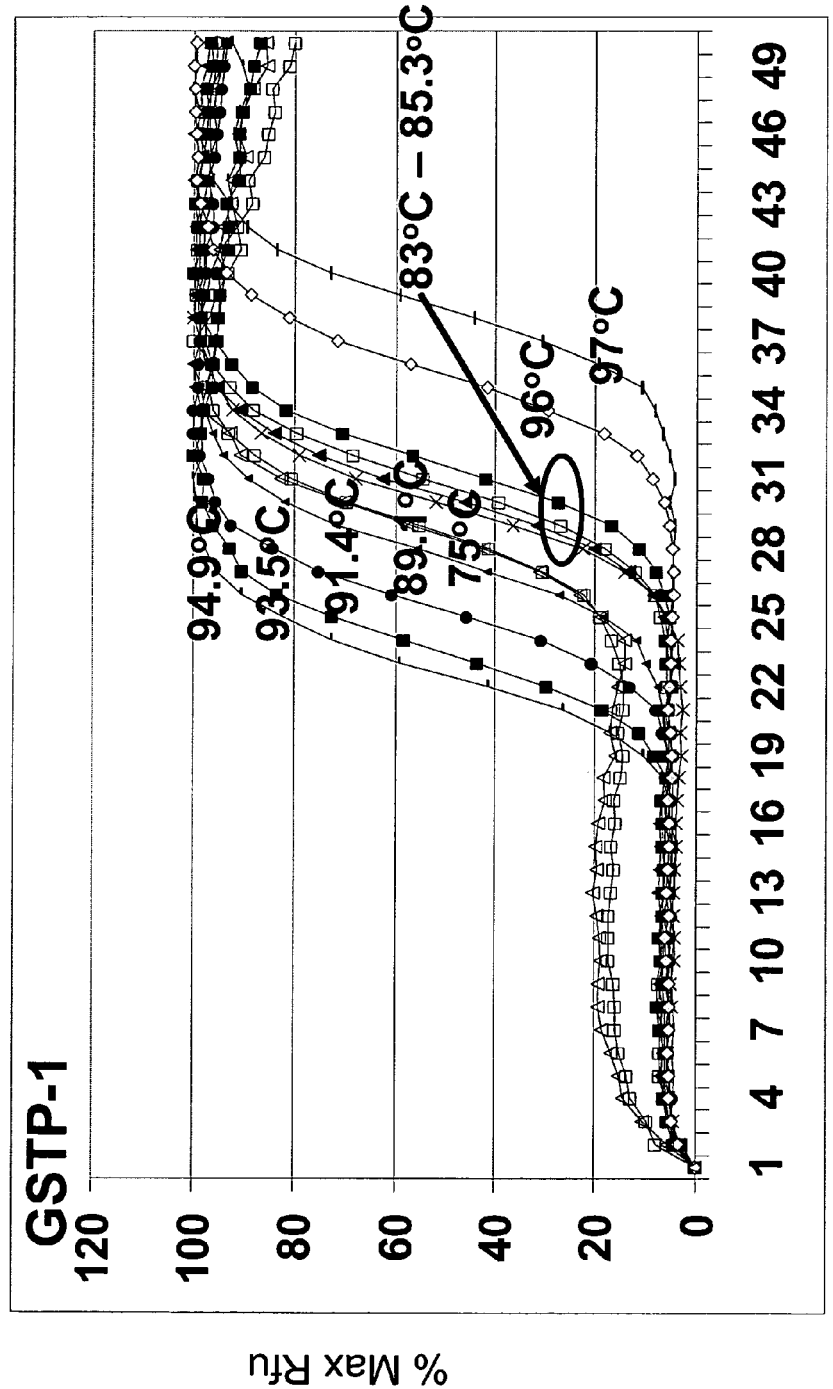
FIGS. 11A-11C illustrate the complex effects of pre-heating to various temperatures Alu I restriction fragments prior to preparation of methylome libraries by ligation of universal adaptor on the relative presence of promoter sequences. Promoter sequences of high, intermediate, or low GC content are analyzed by quantitative PCR as exemplified by the GSTP-1 (FIG. 11A), MDR-1 (FIG. 11B), and APC (FIG. 11C) promoters, respectively. Differential enrichment of library fragments based on their GC content is demonstrated.
Figure 11B:
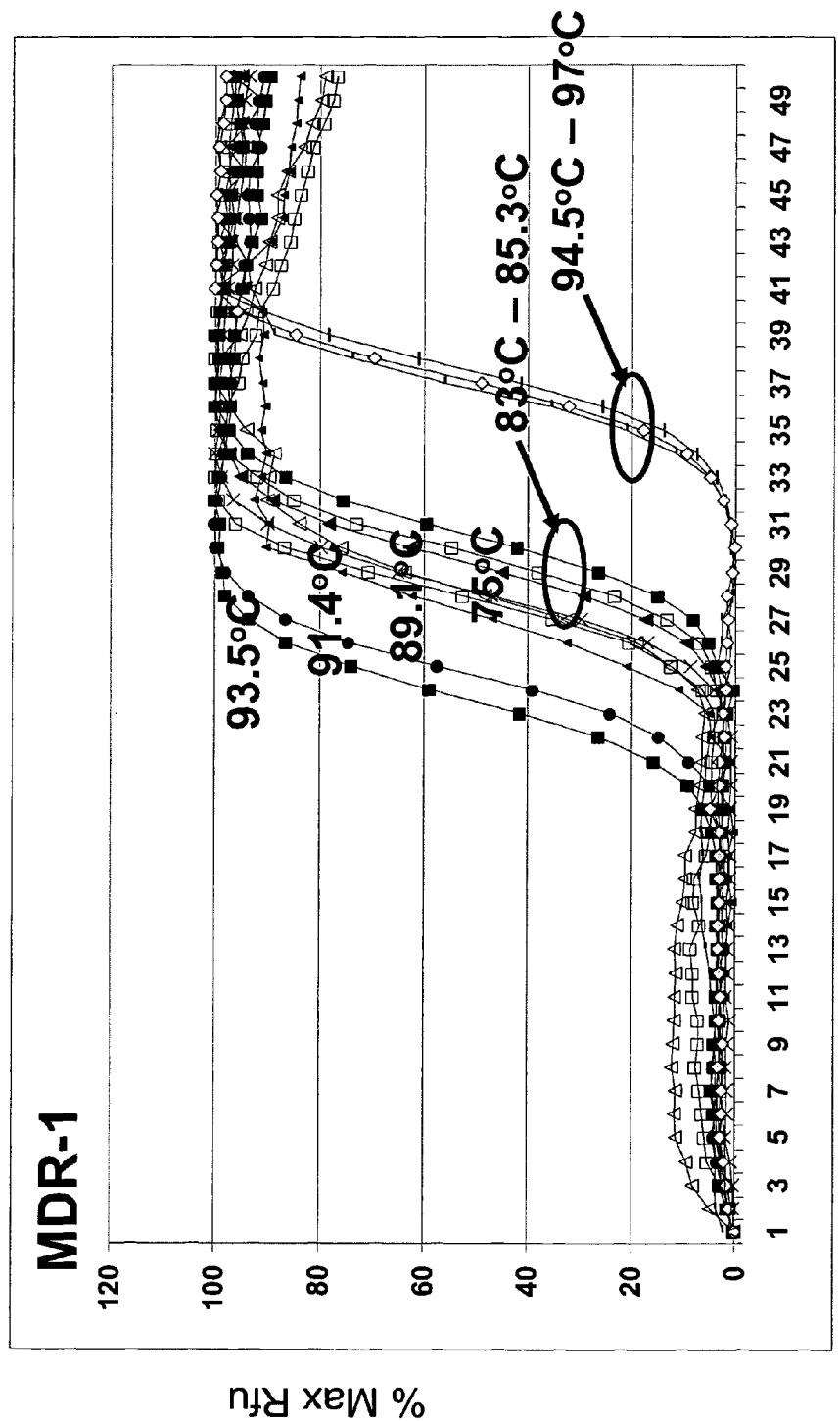
Figure 11C:
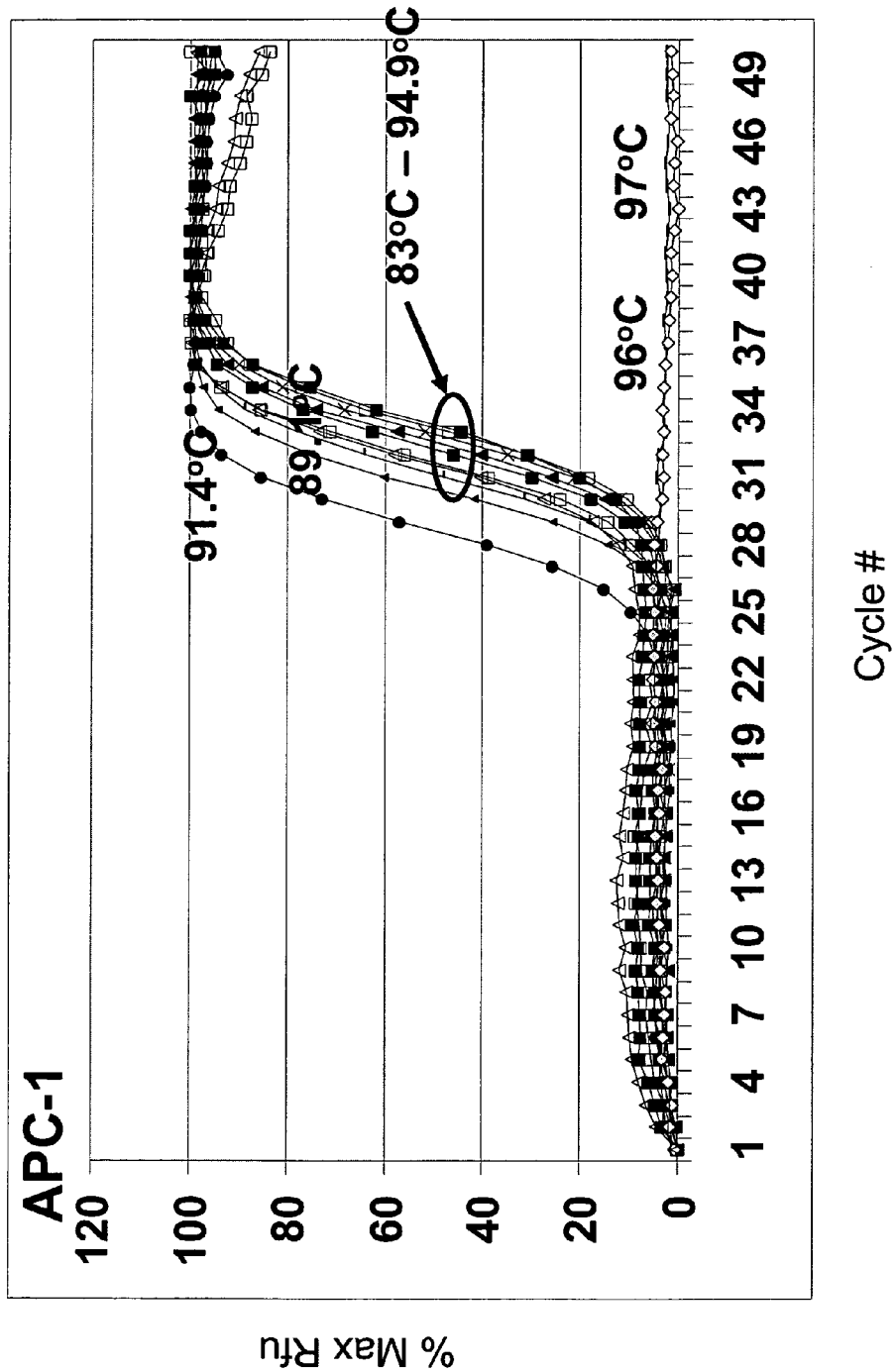

As shown in FIGS. 11A, 11B, and 11C, a complex pattern of temperature-dependent shifts of the amplification curves was observed relative to the control treatment of 75° C. Temperatures of between 89° C. and 94° C. resulted in enrichment of on average 2 to 7 cycles (4- to 128-fold) for promoter sites of high to intermediate GC content (FIGS. 11A and 11B), whereas temperatures between 83° C. and 85° C. resulted in 1-2 cycles (2 to 4 times) le efficient amplification. For the lower GC content in the APC-1 promoter site, the optimal temperature for enrichment was 91.5° C. resulting in about 8-fold enrichment, whereas higher temperatures caused reduced amplification. For all three promoter sites, pre-heating at about 95° C. to 97° C. caused significant reduction of copy number and complete denaturing for the low GC content in the APC promoter site.

Example 2

Enrichment of Libraries Prepared From Cell-Free Urine DNA for Promoter Sequences by Heat Treatment This example demonstrates that methylome libraries prepared from cell-free urine DNA can be enriched for promoter sequences by pre-heating prior to library preparation at temperatures that will selectively denature a fraction of the DNA having low average GC content, thereby making it incompetent for ligation.

Urine samples from healthy donors or from prostate cancer patients were collected in 50 ml Falcon tubes and stabilized for storage by adding 0.1 volume of 0.5 M EDTA. Urine samples were centrifuged at 1,800× g for 10 min at ambient temperature to sediment cells and supernatant was transferred carefully to a fresh tube. An equal volume of 6 M guanidine thiocyanate was added to each sample followed by ⅙ vol of Wizard Miniprep resin (Promega catalog #A7141). DNA was bound to the resin by rotation for 1 hour at ambient temperature. The resin was then sedimented by brief centrifugation at 500× g and loaded on Wizard minicolumns (Promega catalog #A7211)) using syringe barrel extensions after carefully decanting out the supernatant. Resin was washed with 5 ml of wash buffer (Promega catalog # A8102) using Qiagen QIAvac 24 vacuum manifold. Minicolumns were then centrifuged for 2 min at 10,000×g to remove residual wash buffer and bound DNA were eluted with 50μl of DNAse-free water at 10,000×g for 1 min. Eluted DNA was buffered by adding 0.1 vol of 10× TE-L buffer and quantified by fluorescent spectrophotometer using Pico Green (Molecular Probes) and λ phage DNA standards.

Aliquots of 22 ng of purified DNA were either heat-treated directly or processed for enzymatic repair of termini with Klenow fragment of DNA polymerase I before heat treatment.

The first set of samples were heated in duplicate directly for 10 min at 75° C. (control), 89° C., 91° C., or 93° C. in 13 μl of NEBuffer 4 (NEB) followed by cooling on ice.

The second set of samples were first incubated in 1× NEBuffer 4 (NEB) with 0.4 units of Klenow fragment of DNA polymerase I (USB Corporation), 0.1 mg/ml of BSA, and 13.3 μM dNTPs for 15 min at 25° C. followed by 10 min at 75° C. in a final volume of 15 μl After polishing, samples were heated for 10 min at 75° C. (control), 89° C., 91° C., or 93° C., by cooling on ice.

The first set was polished after heating by incubation with 0.4 units of Klenow fragment of DNA polymerase I (USB Corporation), 0.1 mg/ml of BSA, and 13.3 μM dNTPs for 15 min at 25° C. followed by 10 min at 75° C. in a final volume of 15 μl.

Both sets of samples were then ligated to universal blunt-end adaptor in a reaction mixture comprising 1.25 μM K$_U$ adaptor (Table I), 800 units of T4 DNA ligase, and 1 mM ATP in 1× NEBuffer 4 (NEB) added to a final volume of 21 μl. Ligations were carried out for 1 hour at 25° C. followed by 15 min at 75° C.

Half of the first set of samples (treated before polishing) was subjected to digestion with a cocktail of methylation-sensitive restriction enzymes comprising 5.8 units of AciI and HhaI, and 2.9 units of BstUI, HpaII, and Hinp1I (NEB) in 1× NEBuffer 4 for 12 hours at 37° C., followed by 2 hours at 60° C. The second half was incubated in parallel but without restriction enzymes ("uncut" controls).

Libraries were amplified by quantitative real-time PCR by supplementing the reactions with PCR master mix adding to the following final concentrations: 1×Titanium Taq reaction buffer (Clontech), 200 μM of each dNTP, fluorescein calibration dye (1:100,000) and SYBR Green I (1:100,000), 1 μM universal primer K$_U$ (Table I, SEQ ID NO: 15), 4% DMSO, 200 μM 7-deaza-dGTP (Sigma), and 5 units of Titanium Taq polymerase (Clontech) in a final volume of 75 μl. After initial incubation at 75° C. for 15 min to fill-in the recessed 3' ends of the ligated DNA libraries, amplifications were carried out at 95° C. for 3 min, followed by cycling at 94° C. for 15 sec and 65° C. for 2 min on an I-Cycler real-time PCR instrument (Bio-Rad). Amplified libraries were purified using Multi-Screen PCR cleanup system (Millipore) and quantified by optical density reading.

Aliquots of 80 ng of each amplified library were used to analyze promoter sequences for enrichment by Q-PCR in reaction mixtures comprising: 1×Titanium Taq reaction buffer (Clontech), 200 μM of each dNTP, 4% DMSO, 0.5 M betaine, FCD (1:100,000) and SYBR Green I (1:100,000), 200 nM each forward and reverse primer (Table II, SEQ ID NO:13 and SEQ ID NO:14 for GSTP-1 promoter, SEQ ID NO:5 and SEQ ID NO:6 for APC-1 promoter, SEQ ID NO:7 and SEQ ID NO:8 for MDR-1 promoter, SEQ ID NO:11 and SEQ ID NO:12[for CD-44, and Table III, SEQ ID NO:25 and SEQ ID NO:26 for p16 Exon 2), and 1.5 units of Titanium Taq polymerase (Clontech) in a final volume of 15 μ at 95° C. for 3 min followed by 50 cycles at 94° C. for 15 sec and 68° C. for 1 min.

Figure 12A:
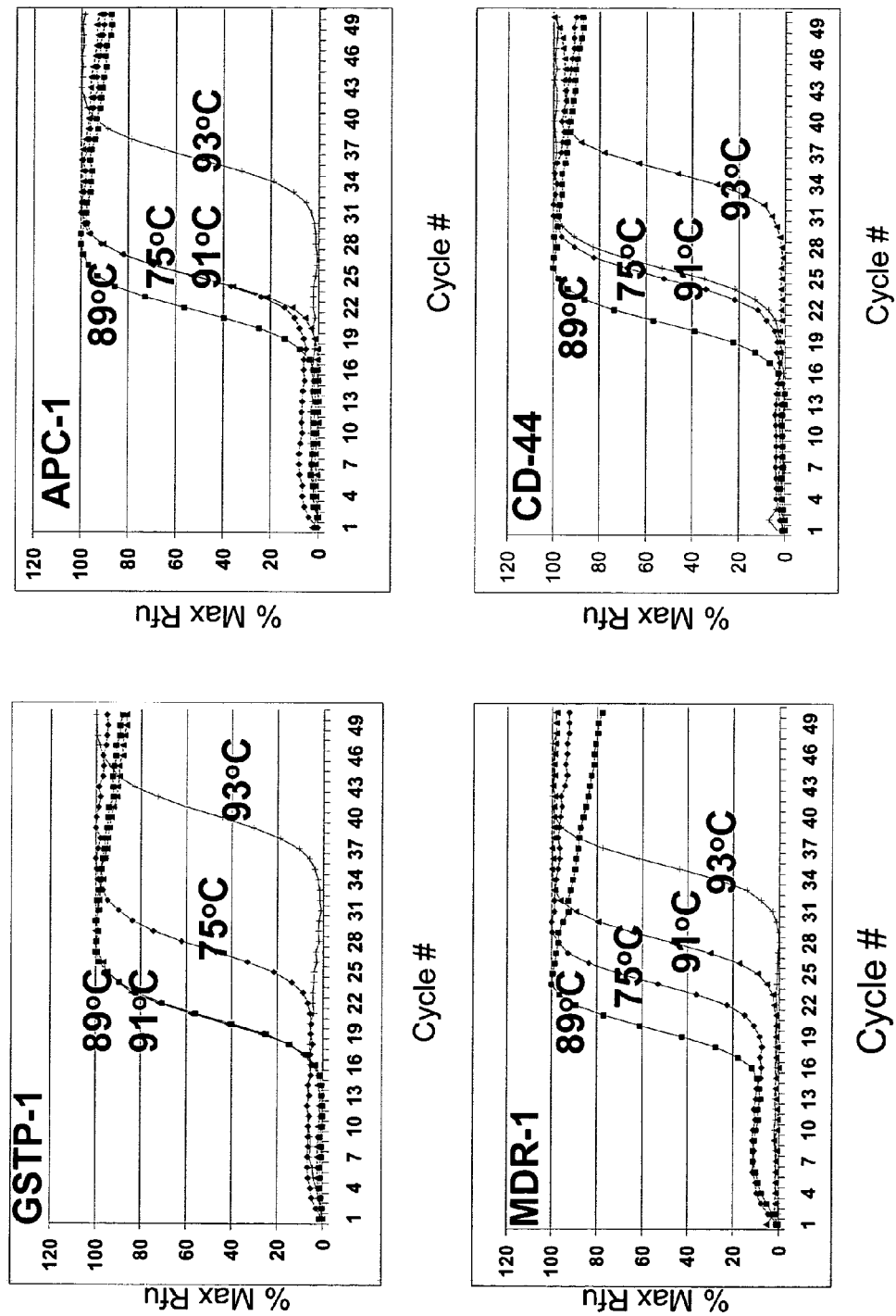
FIGS. 12A and 12B show that methylome libraries prepared from exemplary cell-free urine DNA by ligation of universal adaptor can be enriched for promoter sequences by pre-heating prior to library preparation at temperatures that will selectively denature the fraction of DNA having low to average GC content, thereby making it incompetent for ligation. Maximal enrichment of promoter sites is achieved by pre-heating at 89° C. to 91° C.

FIG. 12A shows the analysis of four promoter sequences in libraries prepared from samples heated after enzymatic repair (set 2 described above). Heat-treatment at 89° C. resulted in maximal enrichment in all tested promoter sites causing a shift between 4 and 7 cycles (16- to 128-fold enrichment), whereas heating at 91° C. resulted in enrichment only for the GC-rich GSTP-1 promoter but had no effect or resulted in delayed amplification for the rest of the promoters. On the other hand, treatment at 93° C. resulted in significant reduction of the copy number of all promoter sites analyzed in cell-free urine DNA libraries.

Figure 12B:
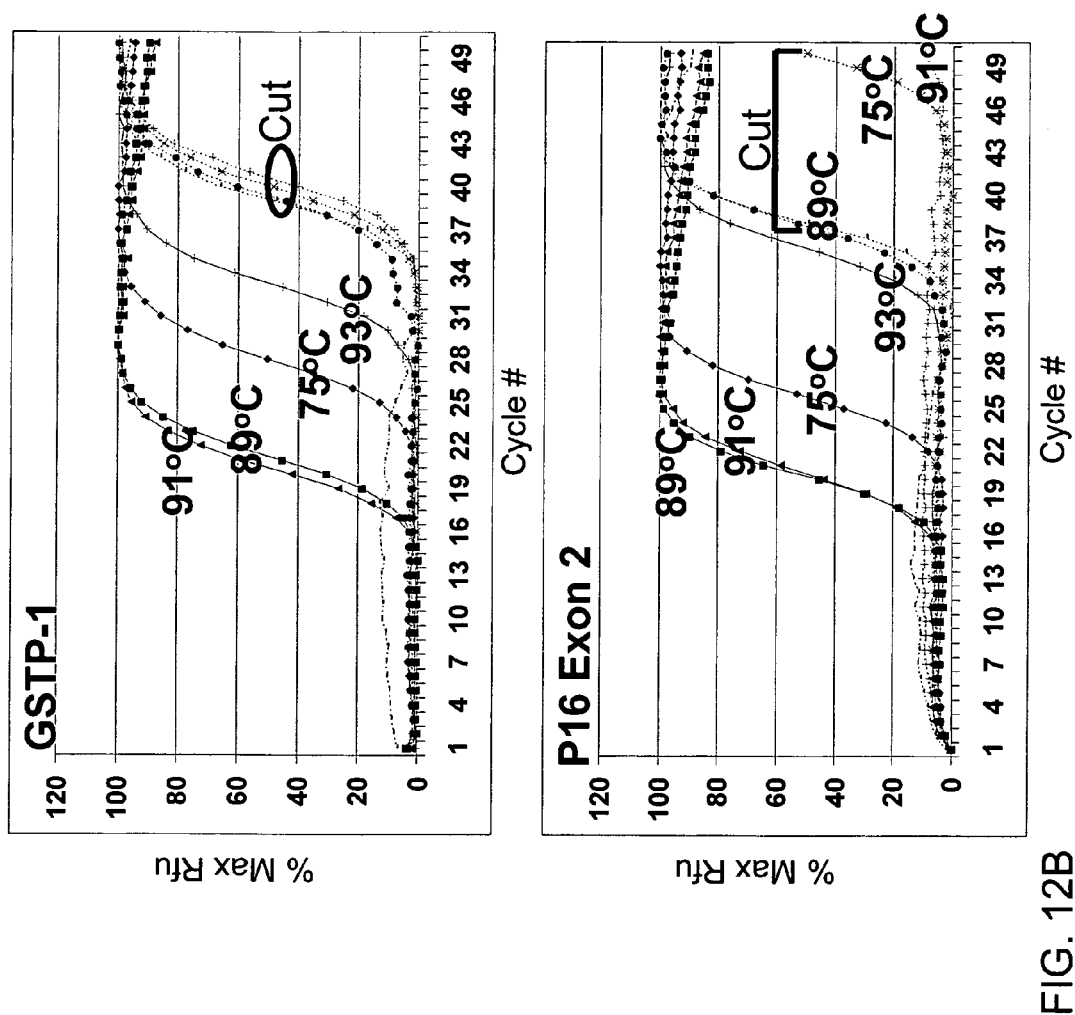

FIG. 12B shows a comparison between heat-treated samples before enzymatic repair (set 1 above) with or without subsequent cleavage with methylation-sensitive restriction enzymes for two CpG islands. As shown, significant enrichment was observed for both CpG islands in libraries pre-treated at 89° C. or 91° C. that were not cut with restriction enzymes. However, no effect of the heat-treatment was found for the samples that were digested with restriction enzymes when the GSTP promoter was analyzed, indicating that the cleavage was complete for this site. On the other hand, when a different CpG site reported to be aberrantly methylated in cancer, p16 Exon 2, was analyzed, both cut and uncut samples were enriched in a similar way by the heat-treatment, suggesting that the enzymatic digestion was perhaps incomplete. In summary, maximal enrichment-of promoter sites in libraries prepared from cell-free urine DNA was obtained after pre-heating at 89° C. to 91° C.

TABLE I

OLIGONUCLEOTIDE ADAPTORS USED FOR PREPARTATION OF GENOMIC AND METHYLOME LIBRARIES FROM ALU-DIGESTED AND URINE HUMAN DNA

| Code | Sequence* | |
|---|---|---|
| Ku Adaptor | 5'-CCAAACACACCCx-3' | (SEQ ID NO: 1) |
| | 3'-GGTTTGTGTGGGTTGTGT-5' | (SEQ ID NO: 2) |
| dU-Hairpin Adaptor | 5'-TGTGTTGGGdUGdUGTGTGGdUdUdUdUdUdUCCACACA CACCCAACACA-3' | (SEQ ID NO: 3)** |
| Mu-1 Primer | 5'-CCACACACACCCAACACA-3' | (SEQ ID NO: 4) |

*x = amino C7 modifier
** dU = deoxy-Uridine

TABLE II

SAMPLE PRIMER PAIRS USED FOR ANALYSIS OF EXEMPLARY ALU-DIGESTED GENOMIC AND URINE METHYLOME LIBRARIES BY REAL-TIME PCR

| Promoter | | Sequence (5'-3') | |
|---|---|---|---|
| APC-1 | F | CGGGTCGGGAAGGGGAGAG | (SEQ ID NO: 5) |
| | R | TGGCGGGCTGCACCAATACAG | (SEQ ID NO: 6) |
| MDR-1 | F | GGGTGGGAGGAAGCATCGTC | (SEQ ID NO: 7) |
| | R | GGTCTCCAGCATCTCCACGAA | (SEQ ID NO: 8) |
| BRCA-1 | F | CCCTTGGTTTCCGTGGCAAC | (SEQ ID NO: 9) |
| | R | CTCCCCAGGGTTCACAACGC | (SEQ ID NO: 10) |
| CD44 | F | CCTCTGCCAGGTTCGGTCC | (SEQ ID NO: 11) |
| | R | GCTGCGTGCCACCAAAACTTGTC | (SEQ ID NO: 12) |
| GSTP-1 | F | TGGGAAAGAGGGAAAGGCTTC | (SEQ ID NO: 13) |
| | B | CCCCAGTGCTGAGTCACGG | (SEQ ID NO: 14) |
| RASSF-1 | F | GCCCAAAGCCAGCGAAGCAC | (SEQ ID NO: 15) |
| | R | CGCCACAGAGGTCGCACCA | (SEQ ID NO: 16) |
| E-Cadherin | F | GCTAGAGGGTCACCGCGT | (SEQ ID NO: 17) |
| | R | CTGAACTGACTTCCGCAAGCTC | (SEQ ID NO: 18) |
| PTGS-2 | F | AGAACTGGCTCTCGGAAGCG | (SEQ ID NO: 19) |
| | R | GGGAGCAGAGGGGGTAGTC | (SEQ ID NO: 20) |
| EDNRB | F | GGGCATCAGGAAGGAGTTTCGAC | (SEQ ID NO: 21) |
| | R | TCGCCAGTATCCACGCTCAA | (SEQ ID NO: 22) |
| P16 Exon 2 | F | GCTTCCTGGACACGCTGGT | (SEQ ID NO: 23) |
| | R | TCTATGCGGGCATGGTTACTG | (SEQ ID NO: 24) |

*F = Forward primer, R = Reverse Primer

TABLE III

SAMPLE PRIMERS USED FOR EXEMPLARY ANALYSIS OF p16 EXON 2

| Promoter | | Sequence (5'-3')* | |
|---|---|---|---|
| P16 (CDKN2A) | F | CAAGCTTCCTTTCCGTCATGCC | (SEQ ID NO: 25) |
| Exon 2 | R | AGCACCACCAGCGTGTCCA | (SEQ ID NO: 26) |

*F = Forward Primer, R = Reverse Primer

REFERENCES

All patents and publications mentioned in the specification are indicative of the levels of those skilled in the art to which the invention pertains. All patents and publications are herein incorporated by reference in their entirety to the same extent as if each individual publication was specifically and individually indicated to be incorporated by reference.

PUBLICATIONS

Antequera, F., and Bird, A., Number of CpG islands and genes in human and mouse. Proc. Natl. Acad. Sci. USA, 190, 11995-11999, (1993).

Bellizzi, D., et al., A procedure for cloning genomic DNA fragments with increasing thermoresistance. Gene, 219, 63-71, (1998).

Clay, O., et al., Compositional heterogeneity within and among isochores in mammalian genomes. I. CsCl and sequence analyses. Gene, 276, 15-24, (2001).

Clay, O., et al., Using analytical ultracentrifugation to study compositional variation in vertebrate genomes. Eur. Biophys. J., 32, 418-426, (2003).

Cross, S. H., and Bird, A. P., CpG islands and genes. Curr. Opin. Genet. Dev., 5, 309-314, (1995).

Cross, S. H., et al., Isolation of CpG islands from large genomic clones. Nucleic Acid Res., 27, 2099-2107, (1999).

Cross, S. H., et al., CpG island libraries from human chromosomes 18 and 22: landmarks for novel genes. Mammalian genome, 11, 373-383, (2000).

Guttann, T., et al., Base composition heterogeneity of mammalian DNAs in CsCl-netropsin density gradient. Nucleic Acid Res., 3, 835-845, (1976).

Ozawa, K., et al., A column gel-electrophoresis-coupled genomic DNA subtractive hybridization technique. Electrophoresis, 25, 2193-2200, (2004).

Shiraishi, M., et al., Preferential isolation of DNA fragments associated with CpG islands. Proc. Natl. Acad. Sci. USA, 92, 4229-4233, (1995).

Shiraishi, M., et al., The isolation of CpG islands from human chromosomal regions 11q13 and Xp22 by segregation of partly melted molecules. Nucleic Acid Res., 26, 5544-5550, (1998).

Shiraishi, M., et al., Isolation of DNA fragments associated with methylated CpG islands in human adenocarcinomas of the lung using a methylated DNA binding column and denaturing gradient gel electrophoresis. Proc. Natl. Acad. Sci. USA, 96, 2913-2918, (1999).

Takai, D., and Jones, P. A., Comprehensive analysis of CpG islands in human Chromosomes 21 and 22. Proc. Natl. Acad. Sci. USA, 99, 3740-3745, (2002).

What is claimed is:

1. A method of amplifying a plurality of GC-rich DNA molecules without cloning, comprising:
   providing a plurality of DNA molecules, said plurality having molecules comprising one or more regions that are GC-poor and having molecules comprising one or more regions that are GC-rich;
   subjecting the plurality of DNA molecules to denaturation and renaturation conditions to substantially denature GC-poor regions but not to denature GC-rich regions, wherein the GC-rich regions are referred to as thermo-resistant DNA molecules;
   attaching an adaptor by ligation to ends of the thermo-resistant DNA molecules to produce adaptor-linked thermo-resistant DNA molecules; and
   performing one of the following without cloning:
   (a) subjecting the adaptor-linked thermo-resistant DNA molecules to one or more methylation-sensitive restriction enzymes, thereby cleaving non-methylated DNA and retaining methylated DNA fragments to produce methylated GC-rich DNA fragments; and
   PCR amplifying the methylated GC-rich DNA fragments; or
   (b) subjecting the adaptor-linked thermo-resistant DNA molecules to one or more methylation-specific restriction enzymes, thereby cleaving methylated DNA and retaining non-methylated DNA fragments to produce non-methylated GC-rich DNA fragments; and
   PCR amplifying the non-methylated GC-rich DNA fragments.

2. The method of claim 1, wherein the conditions to denature GC-poor regions but not to denature GC-rich regions comprise temperature sufficient to denature GC-poor regions but not to denature GC-rich regions, pressure sufficient to denature GC-poor regions but not to denature GC-rich regions, pH sufficient to denature GC-poor regions but not to denature GC-rich regions, organic solvents sufficient to denature GC-poor regions but not to denature GC-rich regions, or a combination thereof.

3. The method of claim 1, wherein the conditions to denature GC-poor regions but not to denature GC-rich regions comprise temperature sufficient to denature GC-poor regions but not to denature GC-rich regions.

4. The method of claim 1, wherein the subjecting the plurality of DNA molecules to sufficient conditions to denature GC-poor regions but not to denature GC-rich regions is further defined as:
   subjecting the plurality to a first temperature such that the GC-poor regions become single-stranded and such that the GC-rich regions are undenatured or are denatured only in part, thereby retaining double stranded form at least in part; and
   subjecting the plurality to a second temperature such that at least part of the GC-poor regions retain single-stranded form and such that at least part of the GC-rich regions maintain or renature to a double-stranded form, thereby producing ligation-competent GC-rich molecules.

5. The method of claim 1, wherein the molecules comprising GC-rich regions are further defined as comprising one or more regions having GC content greater than 50%.

6. The method of claim 4, wherein the first temperature is greater than 60° C.

7. The method of claim 4, wherein the second temperature is lower than 85° C.

8. The method of claim 1, wherein the adaptors are added by ligation and polymerization.

9. The method of claim 8, wherein the ends of the renatured GC-rich molecules are polished prior to said ligating.

10. The method of claim 8, wherein the ligating is further defined as blunt-end ligating.

11. The method of claim 8, wherein the renatured GC-rich molecules are further defined as restriction enzyme fragments, and wherein the adaptors are suitable for ligation onto the respective digested fragment ends.

12. The method of claim 8, wherein the ligating is further defined as ligating with both strands of the DNA molecules and the adaptors.

13. The method of claim 8, wherein the ligating is further defined as ligating with only one strand of each molecule, said one strand being the 5' end of the DNA molecules and the 3' end of the adaptors, wherein the method further comprises 3' extension of a nick in the adaptor-ligated molecules.

14. The method of claim 1, wherein the plurality of DNA molecules is provided is from a body fluid or tissue.

15. The method of claim 1, wherein the plurality of DNA molecules comprise known sequences at the ends of the molecules.

16. The method of claim 1, further comprising determining at least part of the sequence of one or more of the GC-rich amplified molecules.

17. The method of claim 16, wherein the determined sequence comprises a regulatory sequence.

18. The method of claim 16, wherein the determining step provides diagnostic information for an individual.

19. The method of claim 18, wherein the diagnostic information comprises cancer diagnosis information for the individual.

20. The method of claim 1, wherein the GC-rich region comprises at least part of regulatory sequence.

21. The method of claim 1, wherein the GC-rich region comprises at least part of a CpG island.

22. The method of claim 1, further comprising digesting the plurality of DNA molecules with a restriction enzyme.

23. The method of claim 10, wherein the adaptors are ligated to the 5' ends of the thermo-resistant DNA molecules to produce a nick in the adaptor-ligated molecules and wherein the method further comprises polymerization from the 3' end of the nick in the adaptor-ligated molecules.

24. The method of claim 1, wherein the DNA molecules comprise genomic DNA.

25. The method of claim 1, wherein the methylation-sensitive restriction enzyme is Aci I, Acc II, Asp LE I, Ava I, Bce AI, Bsa HI, Bsh 1236 I, Bsi E1, Bsi SI, Bst FN I, Bst HH I, Bst UI, Cfo I, Hap II, Hga I, Hha I, HinP1 I, Hin 6I, Hpa II, Hpy 99I, Hpy CH4 IV, Hsp AI, Mvn I, Ssi, or a combination thereof.

26. The method of claim 1, wherein the methylation-specific restriction enzyme is McrBC.

27. The method of claim 1, wherein the adaptor-linked thermo-resistant DNA molecules, the methylated DNA fragments, or the non-methylated DNA fragments are sequenced.

28. The method of claim 1, wherein the adaptor-linked thermo-resistant DNA molecules, the methylated DNA fragments, or the non-methylated DNA fragments are subject to high throughput analysis.

29. The method of claim 1, wherein the adaptor-linked thermo-resistant DNA molecules, the methylated DNA fragments, or the non-methylated DNA fragments are subject to microarray analysis.

* * * * *

UNITED STATES PATENT AND TRADEMARK OFFICE
CERTIFICATE OF CORRECTION

PATENT NO. : 8,409,804 B2
APPLICATION NO. : 11/367046
DATED : April 2, 2013
INVENTOR(S) : Vladimir L. Makarov et al.

It is certified that error appears in the above-identified patent and that said Letters Patent is hereby corrected as shown below:

In the Claims

Claim 14, column 35, line 2, delete "is provided is" and insert --provided are-- therefor.

Signed and Sealed this
Twenty-sixth Day of November, 2013

Margaret A. Focarino
*Commissioner for Patents of the United States Patent and Trademark Office*